(12) United States Patent
Urquhart et al.

(10) Patent No.: US 7,925,328 B2
(45) Date of Patent: Apr. 12, 2011

(54) METHOD AND APPARATUS FOR PERFORMING STEREOTACTIC SURGERY

(75) Inventors: Steven Urquhart, Minneapolis, MN (US); Richard Schallhorn, Lake Elmo, MN (US)

(73) Assignee: Medtronic Navigation, Inc., Louisville, CO (US)

(*) Notice: Subject to any disclaimer, the term of this patent is extended or adjusted under 35 U.S.C. 154(b) by 577 days.

(21) Appl. No.: 11/958,037

(22) Filed: Dec. 17, 2007

(65) Prior Publication Data
US 2008/0097195 A1 Apr. 24, 2008

Related U.S. Application Data

(63) Continuation of application No. 10/651,267, filed on Aug. 28, 2003, now Pat. No. 7,313,430.

(51) Int. Cl.
*A61B 5/05* (2006.01)
(52) U.S. Cl. .......................... 600/429; 606/130
(58) Field of Classification Search .............. 600/407, 600/411, 417, 424–429; 606/130
See application file for complete search history.

(56) References Cited

U.S. PATENT DOCUMENTS

| | | | |
|---|---|---|---|
| 1,576,781 A | 3/1926 | Phillips | |
| 1,735,726 A | 11/1929 | Bornhardt | |
| 2,407,845 A | 9/1946 | Nemeyer | |
| 2,650,588 A | 9/1953 | Radcliffe | |
| 2,697,433 A | 12/1954 | Zehnder | |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,294,083 A | 12/1966 | Alderson | |
| 3,367,326 A | 2/1968 | Frazier | |
| 3,439,256 A | 4/1969 | Kähne et al. | |
| 3,577,160 A | 5/1971 | White | |
| 3,614,950 A | 10/1971 | Rabey | |
| 3,644,825 A | 2/1972 | Davis, Jr. et al. | |

(Continued)

FOREIGN PATENT DOCUMENTS

CA 964149 3/1975

(Continued)

OTHER PUBLICATIONS

European Search Report mailed Jan. 21, 2010 for EP09180386 filed Dec. 22, 2009 and which claims benefit of EP 040197568, filed Aug. 20, 2004; which claims benefit of U.S. Appl. No. 10/651,267, filed Aug. 28, 2003.

(Continued)

*Primary Examiner* — Brian Casler
*Assistant Examiner* — Parikha S Mehta
(74) *Attorney, Agent, or Firm* — Harness, Dickey

(57) ABSTRACT

A stereotactic navigation system for navigating an instrument to a target within a patient may include a stereotactic head frame, an imaging device, a tracking device, a controller and a display. The stereotactic head frame is coupled to the patient and is used to assist in guiding the instrument to the target. The imaging device captures image data of the patient and of the stereotactic head frame. The tracking device is used to track the position of the instrument relative to the stereotactic head frame. The controller receives the image data from the imaging device and identifies the stereotactic head frame in the image data and automatically registers the image data with navigable patient space upon identifying the stereotactic head frame, while the display displays the image data.

36 Claims, 9 Drawing Sheets

U.S. PATENT DOCUMENTS

| | | |
|---|---|---|
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner et al. |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler et al. |
| 4,396,885 A | 8/1983 | Constant et al. |
| 4,396,945 A | 8/1983 | DiMatteo et al. |
| 4,403,321 A | 9/1983 | Kruger et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen et al. |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple et al. |
| 4,608,977 A | 9/1986 | Brown |
| 4,613,866 A | 9/1986 | Blood |
| 4,617,925 A | 10/1986 | Laitinen et al. |
| 4,618,978 A | 10/1986 | Cosman |
| 4,621,628 A | 11/1986 | Brudermann et al. |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano et al. |
| 4,673,352 A | 6/1987 | Hansen et al. |
| 4,688,037 A | 8/1987 | Krieg |
| 4,701,049 A | 10/1987 | Beckman et al. |
| 4,705,395 A | 11/1987 | Hageniers et al. |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson et al. |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor et al. |
| 4,764,016 A | 8/1988 | Johansson et al. |
| 4,771,787 A | 9/1988 | Wurster et al. |
| 4,779,212 A | 10/1988 | Levy et al. |
| 4,782,239 A | 11/1988 | Hirose et al. |
| 4,788,481 A | 11/1988 | Niwa et al. |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg et al. |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu et al. |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue et al. |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean et al. |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube et al. |
| 5,119,817 A | 6/1992 | Allen |

| | | | | | | |
|---|---|---|---|---|---|---|
| 5,142,930 A | 9/1992 | Allen et al. | | 5,386,828 A | 2/1995 | Owens et al. |
| 5,143,076 A | 9/1992 | Hardy et al. | | 5,389,101 A | 2/1995 | Heilbrun et al. |
| 5,152,288 A | 10/1992 | Hoenig et al. | | 5,391,199 A | 2/1995 | Ben-Haim et al. |
| 5,160,337 A | 11/1992 | Cosman | | 5,394,457 A | 2/1995 | Leibinger et al. |
| 5,161,536 A | 11/1992 | Vilkomerson et al. | | 5,394,875 A | 3/1995 | Lewis et al. |
| 5,178,164 A | 1/1993 | Allen | | 5,397,329 A | 3/1995 | Allen |
| 5,178,621 A | 1/1993 | Cook et al. | | 5,398,684 A | 3/1995 | Hardy |
| 5,186,174 A | 2/1993 | Schlondorff et al. | | 5,399,146 A | 3/1995 | Nowacki et al. |
| 5,187,475 A | 2/1993 | Wagener et al. | | 5,400,384 A | 3/1995 | Fernandes et al. |
| 5,188,126 A | 2/1993 | Fabian et al. | | 5,402,801 A | 4/1995 | Taylor |
| 5,190,059 A | 3/1993 | Fabian et al. | | 5,408,409 A | 4/1995 | Glassman et al. |
| 5,193,106 A | 3/1993 | DeSena | | 5,413,573 A | 5/1995 | Koivukangas et al. |
| 5,197,476 A | 3/1993 | Nowacki et al. | | 5,417,210 A | 5/1995 | Funda et al. |
| 5,197,965 A | 3/1993 | Cherry et al. | | 5,419,325 A | 5/1995 | Dumoulin et al. |
| 5,198,768 A | 3/1993 | Keren et al. | | 5,423,334 A | 6/1995 | Jordan |
| 5,198,877 A | 3/1993 | Schulz | | 5,425,367 A | 6/1995 | Shapiro et al. |
| 5,207,688 A | 5/1993 | Carol | | 5,425,382 A | 6/1995 | Golden et al. |
| 5,211,164 A | 5/1993 | Allen | | 5,426,683 A | 6/1995 | O'Farrell, Jr. et al. |
| 5,211,165 A | 5/1993 | Dumoulin et al. | | 5,426,687 A | 6/1995 | Goodall et al. |
| 5,211,176 A | 5/1993 | Ishiguro et al. | | 5,427,097 A | 6/1995 | Depp |
| 5,212,720 A | 5/1993 | Landi et al. | | 5,429,132 A | 7/1995 | Guy et al. |
| 5,214,615 A | 5/1993 | Bauer et al. | | 5,433,198 A | 7/1995 | Desai |
| 5,219,351 A | 6/1993 | Teubner et al. | | RE35,025 E | 8/1995 | Anderton |
| 5,222,499 A | 6/1993 | Allen et al. | | 5,437,277 A | 8/1995 | Dumoulin et al. |
| 5,224,049 A | 6/1993 | Mushabac | | 5,443,066 A | 8/1995 | Dumoulin et al. |
| 5,228,442 A | 7/1993 | Imran | | 5,443,489 A | 8/1995 | Ben-Haim et al. |
| 5,230,338 A | 7/1993 | Allen et al. | | 5,444,756 A | 8/1995 | Pai et al. |
| 5,230,623 A | 7/1993 | Guthrie et al. | | 5,445,144 A | 8/1995 | Wodicka et al. |
| 5,233,990 A | 8/1993 | Barnea | | 5,445,150 A | 8/1995 | Dumoulin et al. |
| 5,237,996 A | 8/1993 | Waldman et al. | | 5,445,166 A | 8/1995 | Taylor |
| 5,249,581 A | 10/1993 | Horbal et al. | | 5,446,548 A | 8/1995 | Gerig et al. |
| 5,251,127 A | 10/1993 | Raab | | 5,447,154 A | 9/1995 | Cinquin et al. |
| 5,251,635 A | 10/1993 | Dumoulin et al. | | 5,448,610 A | 9/1995 | Yamamoto et al. |
| 5,253,647 A | 10/1993 | Takahashi et al. | | 5,453,686 A | 9/1995 | Anderson |
| 5,255,680 A | 10/1993 | Darrow et al. | | 5,456,718 A | 10/1995 | Szymaitis |
| 5,257,636 A | 11/1993 | White | | 5,457,641 A | 10/1995 | Zimmer et al. |
| 5,257,998 A | 11/1993 | Ota et al. | | 5,458,718 A | 10/1995 | Venkitachalam et al. |
| 5,261,404 A | 11/1993 | Mick et al. | | 5,464,446 A | 11/1995 | Dreessen et al. |
| 5,265,610 A | 11/1993 | Darrow et al. | | 5,469,847 A | 11/1995 | Zinreich et al. |
| 5,265,611 A | 11/1993 | Hoenig et al. | | 5,478,341 A | 12/1995 | Cook et al. |
| 5,269,759 A | 12/1993 | Hernandez et al. | | 5,478,343 A | 12/1995 | Ritter et al. |
| 5,271,400 A | 12/1993 | Dumoulin et al. | | 5,480,422 A | 1/1996 | Ben-Haim et al. |
| 5,273,025 A | 12/1993 | Sakiyama et al. | | 5,480,439 A | 1/1996 | Bisek et al. |
| 5,274,551 A | 12/1993 | Corby, Jr. | | 5,483,961 A | 1/1996 | Kelly et al. |
| 5,279,309 A | 1/1994 | Taylor et al. | | 5,485,849 A | 1/1996 | Panescu et al. |
| 5,285,787 A | 2/1994 | Machida et al. | | 5,487,391 A | 1/1996 | Panescu |
| 5,291,199 A | 3/1994 | Overman et al. | | 5,487,729 A | 1/1996 | Avellanet et al. |
| 5,291,889 A | 3/1994 | Kenet et al. | | 5,487,757 A | 1/1996 | Truckai et al. |
| 5,295,483 A | 3/1994 | Nowacki et al. | | 5,490,196 A | 2/1996 | Rudich et al. |
| 5,297,549 A | 3/1994 | Beatty et al. | | 5,494,034 A | 2/1996 | Schlondorff et al. |
| 5,299,253 A | 3/1994 | Wessels | | 5,503,416 A | 4/1996 | Aoki et al. |
| 5,299,254 A | 3/1994 | Dancer et al. | | 5,513,637 A | 5/1996 | Twiss et al. |
| 5,299,288 A | 3/1994 | Glassman et al. | | 5,514,146 A | 5/1996 | Lam et al. |
| 5,300,080 A | 4/1994 | Clayman et al. | | 5,515,160 A | 5/1996 | Schulz et al. |
| 5,305,091 A | 4/1994 | Gelbart et al. | | 5,517,990 A | 5/1996 | Kalfas et al. |
| 5,305,203 A | 4/1994 | Raab et al. | | 5,528,651 A * | 6/1996 | Leksell et al. .................. 378/65 |
| 5,306,271 A | 4/1994 | Zinreich et al. | | 5,531,227 A | 7/1996 | Schneider |
| 5,307,072 A | 4/1994 | Jones, Jr. | | 5,531,520 A | 7/1996 | Grimson et al. |
| 5,309,913 A | 5/1994 | Kormos et al. | | 5,542,938 A | 8/1996 | Avellanet et al. |
| 5,315,630 A | 5/1994 | Sturm et al. | | 5,543,951 A | 8/1996 | Moehrmann et al. |
| 5,316,024 A | 5/1994 | Hirschi et al. | | 5,546,940 A | 8/1996 | Panescu et al. |
| 5,318,025 A | 6/1994 | Dumoulin et al. | | 5,546,949 A | 8/1996 | Frazin et al. |
| 5,320,111 A | 6/1994 | Livingston | | 5,546,951 A | 8/1996 | Ben-Haim et al. |
| 5,325,728 A | 7/1994 | Zimmerman et al. | | 5,551,429 A | 9/1996 | Fitzpatrick et al. |
| 5,325,873 A | 7/1994 | Hirschi et al. | | 5,558,091 A | 9/1996 | Acker et al. |
| 5,329,944 A | 7/1994 | Fabian et al. | | 5,566,681 A | 10/1996 | Manwaring et al. |
| 5,330,485 A | 7/1994 | Clayman et al. | | 5,568,384 A | 10/1996 | Robb et al. |
| 5,333,168 A | 7/1994 | Fernandes et al. | | 5,568,809 A | 10/1996 | Ben-haim et al. |
| 5,353,795 A | 10/1994 | Souza et al. | | 5,572,999 A | 11/1996 | Funda et al. |
| 5,353,800 A | 10/1994 | Pohndorf et al. | | 5,573,533 A | 11/1996 | Strul |
| 5,353,807 A | 10/1994 | DeMarco | | 5,575,794 A | 11/1996 | Walus et al. |
| 5,359,417 A | 10/1994 | Muller et al. | | 5,575,798 A | 11/1996 | Koutrouvelis |
| 5,368,030 A | 11/1994 | Zinreich et al. | | 5,583,909 A | 12/1996 | Hanover |
| 5,371,778 A | 12/1994 | Yanof et al. | | 5,588,430 A | 12/1996 | Bova et al. |
| 5,375,596 A | 12/1994 | Twiss et al. | | 5,590,215 A | 12/1996 | Allen |
| 5,377,678 A | 1/1995 | Dumoulin et al. | | 5,592,939 A | 1/1997 | Martinelli |
| 5,383,454 A | 1/1995 | Bucholz | | 5,595,193 A | 1/1997 | Walus et al. |
| 5,385,146 A | 1/1995 | Goldreyer | | 5,596,228 A | 1/1997 | Anderton et al. |
| 5,385,148 A | 1/1995 | Lesh et al. | | 5,600,330 A | 2/1997 | Blood |

| Patent No. | Date | Inventor |
|---|---|---|
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa et al. |
| 5,647,361 A | 7/1997 | Damadian |
| 5,660,185 A | 8/1997 | Shmulewitz et al. |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim et al. |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf et al. |
| 5,702,406 A | 12/1997 | Vilsmeier et al. |
| 5,711,299 A | 1/1998 | Manwaring et al. |
| 5,713,946 A | 2/1998 | Ben-Haim et al. |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim et al. |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais et al. |
| RE35,816 E | 6/1998 | Schulz |
| 5,758,667 A | 6/1998 | Slettenmark et al. |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman et al. |
| 5,769,789 A | 6/1998 | Wang et al. |
| 5,769,843 A | 6/1998 | Abela et al. |
| 5,769,861 A | 6/1998 | Vilsmeier et al. |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon et al. |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn et al. |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson et al. |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim et al. |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno et al. |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz et al. |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab et al. |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,571 A | 9/1999 | Audette et al. |
| 5,954,647 A | 9/1999 | Bova et al. |
| 5,954,796 A | 9/1999 | McCarty et al. |
| 5,957,844 A | 9/1999 | Dekel et al. |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf et al. |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,009,212 A | 12/1999 | Miller et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim et al. |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette et al. |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |

| | | | | | | |
|---|---|---|---|---|---|---|
| 6,131,396 | A | 10/2000 | Duerr et al. | EP | 0319844 | 6/1989 |
| 6,139,183 | A | 10/2000 | Graumann et al. | EP | 0326768 | 8/1989 |
| 6,147,480 | A | 11/2000 | Osadchy et al. | EP | 0350996 | 1/1990 |
| 6,149,592 | A | 11/2000 | Yanof et al. | EP | 0419729 | 4/1991 |
| 6,156,067 | A | 12/2000 | Bryan et al. | EP | 0427358 | 5/1991 |
| 6,161,032 | A | 12/2000 | Acker | EP | 0456103 | 11/1991 |
| 6,165,181 | A | 12/2000 | Heilbrun et al. | EP | 0581704 | 2/1994 |
| 6,167,296 | A | 12/2000 | Shahidi | EP | 0651968 | 5/1995 |
| 6,172,499 | B1 | 1/2001 | Ashe | EP | 0655138 | 5/1995 |
| 6,175,756 | B1 | 1/2001 | Ferre et al. | EP | 0894473 | 2/1999 |
| 6,178,345 | B1 | 1/2001 | Vilsmeier et al. | EP | 0908146 | 4/1999 |
| 6,194,639 | B1 | 2/2001 | Botella et al. | EP | 0930046 | 7/1999 |
| 6,201,387 | B1 | 3/2001 | Govari et al. | FR | 2417970 | 9/1979 |
| 6,203,497 | B1 | 3/2001 | Dekel et al. | FR | 2618211 | 1/1989 |
| 6,211,666 | B1 | 4/2001 | Acker | GB | 2094590 | 9/1982 |
| 6,223,067 | B1 | 4/2001 | Vilsmeier et al. | GB | 2164856 | 4/1986 |
| 6,226,418 | B1 | 5/2001 | Miller et al. | JP | 62-327 | 6/1983 |
| 6,233,476 | B1 | 5/2001 | Strommer et al. | JP | 61-94639 | 5/1986 |
| 6,241,725 | B1 | 6/2001 | Cosman | JP | 63-240851 | 6/1988 |
| 6,246,231 | B1 | 6/2001 | Ashe | JP | 2765738 | 6/1988 |
| 6,259,942 | B1 | 7/2001 | Westermann et al. | JP | 3267054 | 11/1991 |
| 6,273,896 | B1 | 8/2001 | Franck et al. | WO | WO-8809151 | 12/1988 |
| 6,285,902 | B1 | 9/2001 | Kienzle, III et al. | WO | WO-8905123 | 6/1989 |
| 6,298,262 | B1 | 10/2001 | Franck et al. | WO | WO-9005494 | 5/1990 |
| 6,314,310 | B1 | 11/2001 | Ben-Haim et al. | WO | WO-9103982 | 4/1991 |
| 6,332,089 | B1 | 12/2001 | Acker et al. | WO | WO-9104711 | 4/1991 |
| 6,341,231 | B1 | 1/2002 | Ferre et al. | WO | WO-9107726 | 5/1991 |
| 6,351,659 | B1 | 2/2002 | Vilsmeier et al. | WO | WO-9203090 | 3/1992 |
| 6,424,856 | B1 | 7/2002 | Vilsmeier et al. | WO | WO-9206645 | 4/1992 |
| 6,427,314 | B1 | 8/2002 | Acker | WO | WO-9404938 | 3/1994 |
| 6,428,547 | B1 | 8/2002 | Vilsmeier et al. | WO | WO-9423647 | 10/1994 |
| 6,434,415 | B1 | 8/2002 | Foley et al. | WO | WO-9424933 | 11/1994 |
| 6,437,567 | B1 | 8/2002 | Schenck et al. | WO | WO-9507055 | 3/1995 |
| 6,445,943 | B1 | 9/2002 | Ferre et al. | WO | WO-9611624 | 4/1996 |
| 6,470,207 | B1 | 10/2002 | Simon et al. | WO | WO-9632059 | 10/1996 |
| 6,474,341 | B1 | 11/2002 | Hunter et al. | WO | WO-9729683 | 8/1997 |
| 6,478,802 | B2 | 11/2002 | Kienzle, III et al. | WO | WO-9736192 | 10/1997 |
| 6,484,049 | B1 | 11/2002 | Seeley et al. | WO | WO-9740766 | 11/1997 |
| 6,490,475 | B1 | 12/2002 | Seeley et al. | WO | WO-9749453 | 12/1997 |
| 6,493,573 | B1 | 12/2002 | Martinelli et al. | WO | WO-9808554 | 3/1998 |
| 6,498,944 | B1 | 12/2002 | Ben-Haim et al. | WO | WO-9838908 | 9/1998 |
| 6,499,488 | B1 | 12/2002 | Hunter et al. | WO | WO-9915097 | 4/1999 |
| 6,516,046 | B1 | 2/2003 | Frohlich et al. | WO | WO-9921498 | 5/1999 |
| 6,516,213 | B1 | 2/2003 | Nevo et al. | WO | WO-9923956 | 5/1999 |
| 6,527,443 | B1 | 3/2003 | Vilsmeier et al. | WO | WO-9926549 | 6/1999 |
| 6,546,277 | B1 | 4/2003 | Franck et al. | WO | WO-9927839 | 6/1999 |
| 6,551,325 | B2 | 4/2003 | Neubauer et al. | WO | WO-9929253 | 6/1999 |
| 6,584,174 | B2 | 6/2003 | Schubert et al. | WO | WO-9933406 | 7/1999 |
| 6,609,022 | B2 | 8/2003 | Vilsmeier et al. | WO | WO-9937208 | 7/1999 |
| 6,611,700 | B1 | 8/2003 | Vilsmeier et al. | WO | WO-9938449 | 8/1999 |
| 6,640,128 | B2 | 10/2003 | Vilsmeier et al. | WO | WO-9952094 | 10/1999 |
| 6,694,162 | B2 | 2/2004 | Hartlep et al. | WO | WO-9960939 | 12/1999 |
| 6,701,179 | B1 | 3/2004 | Martinelli et al. | WO | WO-0130437 | 5/2001 |
| 6,738,656 | B1 | 5/2004 | Ferre et al. | | | |
| 6,774,624 | B2 * | 8/2004 | Anderson et al. ........ 324/207.17 | | | |
| 2001/0007918 | A1 | 7/2001 | Vilsmeier et al. | | | |
| 2001/0027271 | A1 | 10/2001 | Franck et al. | | | |
| 2002/0032380 | A1 | 3/2002 | Acker et al. | | | |
| 2002/0095081 | A1 | 7/2002 | Vilsmeier | | | |
| 2002/0156363 | A1 | 10/2002 | Hunter et al. | | | |
| 2004/0024309 | A1 | 2/2004 | Ferre et al. | | | |

FOREIGN PATENT DOCUMENTS

| | | |
|---|---|---|
| DE | 3042343 | 6/1982 |
| DE | 3508730 | 9/1986 |
| DE | 3717871 | 12/1988 |
| DE | 3831278 | 3/1989 |
| DE | 3838011 | 7/1989 |
| DE | 4213426 | 10/1992 |
| DE | 4225112 | 12/1993 |
| DE | 4233978 | 4/1994 |
| DE | 19715202 | 10/1998 |
| DE | 19751761 | 10/1998 |
| DE | 19832296 | 2/1999 |
| DE | 19747427 | 5/1999 |
| DE | 10085137 | 11/2002 |
| EP | 0062941 | 10/1982 |
| EP | 0119660 | 9/1984 |
| EP | 0155857 | 9/1985 |

OTHER PUBLICATIONS

"Prestige Cervical Disc System Surgical Technique", 12 pgs., date unknown.

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick, "Distal Locking Screw Insertion Using a Cannulated Drill Bit: Technical Note," Journal of Orthopaedic Trauma, vol. 7, No. 3, 1993, pp. 248-251.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology .COPYRGT. J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).
Champleboux et al., "Accurate Calibration of Cameras and Range Imaging Sensors: The NPBS Method," IEEE International Conference on Robotics and Automation, Nice, France, May, 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions,"International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Co-pending U.S. Appl. No. 09/733,055, filed Dec. 11, 2000 entitled "Method and Apparatus for Cross-Modality Image Registration".
Co-pending U.S. Appl. No. 10/354,562, filed Jan. 30, 2003 entitled "Six Degree of Fredom Alignment Display for Medical Procedures".
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley, "The StealthStation: Three-Dimensional Image-Interactive Guidance for the Spine Surgeon," Spinal Frontiers, Apr. 1996, pp. 7-9.
Foley, et al., "Image-guided Intraoperative Spinal Localization," Intraoperative Neuroprotection, Chapter 19, 1996, pp. 325-340.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (undated.

Germano, "Instrumentation, Technique and Technology", Neurosurgery, vol. 37, No. 2, Aug. 1995, pp. 348-350.
Gildenberg et al., "Calculation of Sterotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (undated.
Hamadeh et al, "Kinematic Study of Lumbar Spine Using Functional Radiographies and 3D/2D Registration," TIMC UMR 5525—IMAG (1997).
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-366 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Sterotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Sterotaxis," Surg. Neurol., 1985, pp. 559-566.

Laitinen, "Nonivnasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble, (1995).

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee, "VI Adaption de la Methodologie a Quelques Applications Cliniques," Chapitre VI, pp. 133-148, date unknown.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96, date unknown.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefa.alpha.mi.alpha.bildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Roberts et al., "A frameless sterotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Sterotactic System, E2-E6, date unknown.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128, (1997).

Hamadeh et al., "Automated 3-Dimensional Computed Tomographic and Fluorscopic Image Registration," Computer Aided Surgery (1998), 3:11-19.

Partial European Search Report completed Nov. 30, 2004, mailed Dec. 30, 2004.

Partial European Search Report dated Dec. 30, 2004.

* cited by examiner

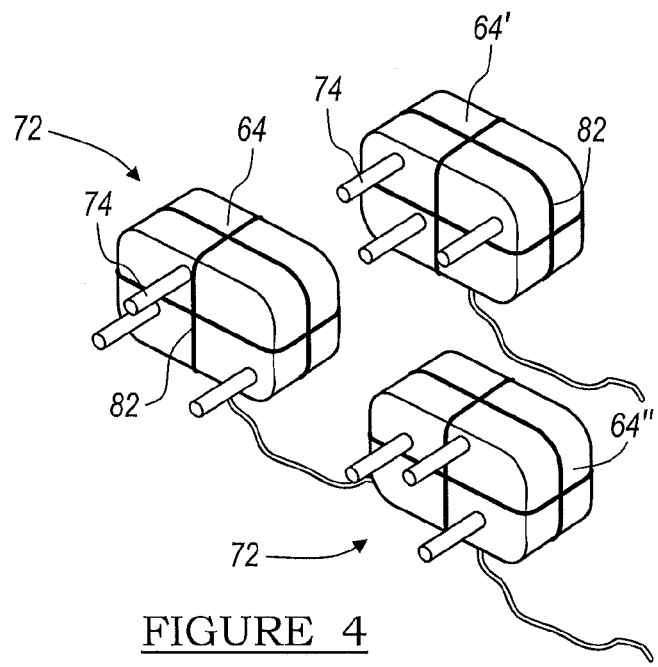
FIGURE 4
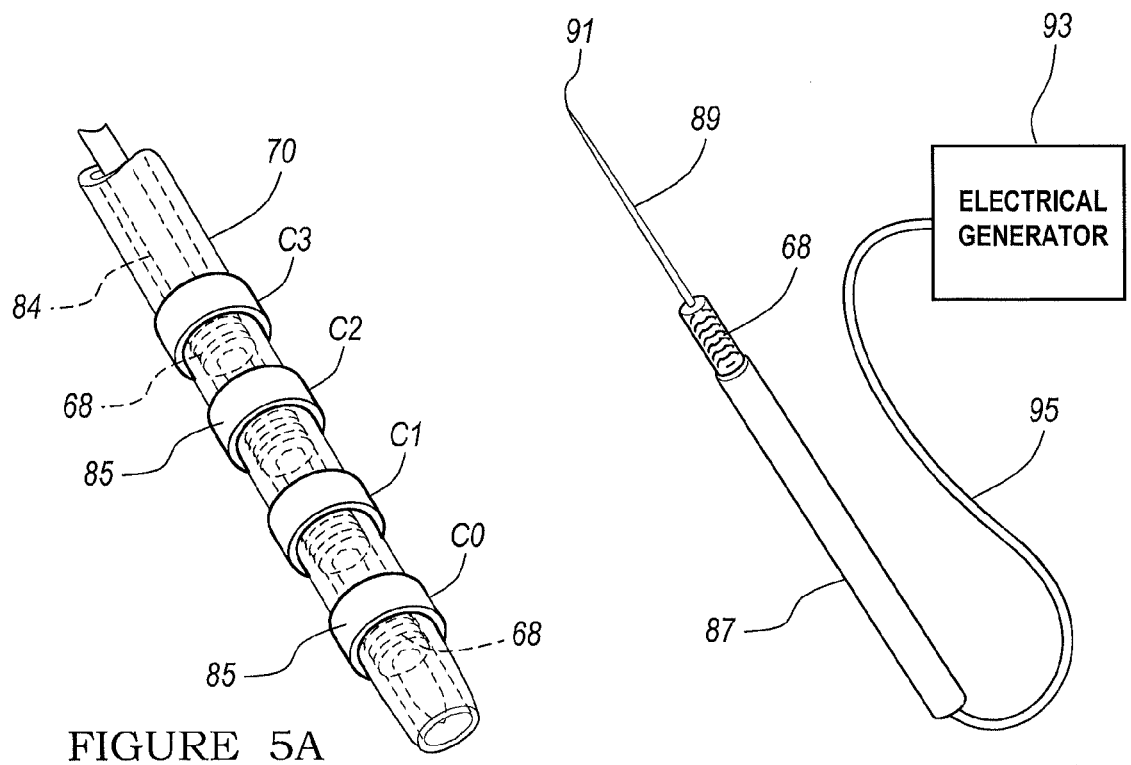
FIGURE 5A
FIGURE 5B

METHOD AND APPARATUS FOR PERFORMING STEREOTACTIC SURGERY

CROSS-REFERENCE TO RELATED APPLICATION

This application is a continuation of U.S. patent application Ser. No. 10/651,267 filed on Aug. 28, 2003, now U.S. Pat. No. 7,313,430, issued on Dec. 25, 2007. The disclosure of the above application is incorporated herein by reference.

FIELD OF THE INVENTION

The present invention relates generally to stereotactic surgery, and more specifically, to a method and apparatus for performing stereotactic surgery utilizing image guidance.

BACKGROUND OF THE INVENTION

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), isocentric C-arm fluoroscopic imaging, positron emission tomography (PET), and ultrasound imaging (US) has increased the interest in image guided medical procedures.

Typically during neurological procedures, stereotactic guidance, sometimes referred to as stereotaxy, is employed by a physician to reach a target site. Stereotaxy is generally defined as the ability to locate and access an object in three-dimensional space. Stereotaxy is further characterized by surgical delivery of an instrument guided by the use of three-dimensional scanning techniques, such as computed tomography (CT) or magnetic resonance imaging (MRI). Typically, stereotaxy procedures require the use of a stereotactic head frame, which is generally referred to as a frame-based stereotaxy procedure. A typical stereotactic head frame is a halo-like device that is rigidly affixed to the patient's skull under local anesthesia, generally using four pins or screws, Once the stereotactic frame is secured, the stereotactic frame is used to define a target and a trajectory to the target, identified with the CT or MRI images. The stereotactic frame may also act as a guide for delivering various types of instruments, such as a biopsy needle or DBS leads or electrodes.

However, use of stereotactic frames may sometimes pose disadvantages. For example, to insure that the instrument guided by the stereotactic frame has reached the appropriate target, two-dimensional fluoroscopic images may be taken intra-procedurally to allow a physician to visualize the location of the instrument being advanced through the neuro structure. However, use of such fluoroscopic imaging throughout a procedure exposes both the patient and the operating room staff to radiation. Therefore, the number of fluoroscopic images taken during a procedure is preferably limited to reduce the radiation exposure to the patient and staff. Optimally, the fluoroscopic imaging would be limited to verifying that an instrument has reached the target site.

In order to adjust a stereotactic frame, the stereotactic frame typically includes various graduations or indentations that are scaled to provide separate discreet movements along the scale or vernier caliper of the stereotactic frame. Thus, the graduations on the stereotactic frame may limit the freedom or range of motion for targeting and trajectory path of the instrument, since they may only be set between individual discreet points. Moreover, stereotactic frames may warp or bend after many years of use. This may result in inaccurate targeting and trajectories that may be unknown to a surgeon performing the procedure. Also, eliminating the graduations on the scale, eliminates motion constraints, thereby providing more precise and infinite freedom of movement for targeting and aligning instrument trajectories.

Additionally, there is generally a base of knowledge which must be acquired in order to use a conventional stereotactic frame, thereby enabling the frame to be properly positioning for the target and trajectory. In this regard, the target and trajectory adjustments are typically manually adjusted via adjustment knobs positioned on the stereotactic frame following various calculations that generally must be made in order to direct the instrument to the appropriate target. This manual adjustment of the various scales to adjust the x, y, and z coordinates, as well as the rotations about these coordinates for targeting and trajectory are susceptible to human error. Moreover, in some situations the stereotactic frame may be put in backwards or incorrectly due to human error.

An image guided surgical navigation system that enables the physician to see the location of an instrument relative to a patient's anatomy, without the need to acquire real-time fluoroscopic images throughout the surgical procedure is disclosed in U.S. Pat. No. 6,470,207, entitled "Navigational Guidance Via Computer-Assisted Fluoroscopic Imaging", issued Oct. 22, 2002, which is hereby incorporated by reference in its entirety. In this system, representations of surgical instruments are overlaid on preacquired fluoroscopic images of the patient, based on the position of the instruments determined by a tracking sensor associated with the instruments. However, typical navigation systems generally require dynamic reference frames to track the position of the patient should patient movement occur during the procedure and also require manual registration in order to register localized preacquired images with the surgical patient space. These procedures may sometimes be time consuming and require a knowledge of surgical navigation procedures.

It is, therefore, desirable to provide a method and apparatus for performing stereotactic surgery in a more accurate and efficient manner, which does not suffer from the above-mentioned disadvantages. It is also an object of the present invention to provide such a method and apparatus for performing stereotactic surgery that provides more precise targeting and trajectory alignment, more freedom of movement, more accuracy and efficiency, automatic registration, automatic setting of the target and trajectory, reduces or eliminates the need for interoperative fluoroscopic imaging and ease of use.

SUMMARY OF THE INVENTION

A method and apparatus for performing stereotactic surgery using a stereotactic navigation system is disclosed. The method and apparatus employs a stereotactic head frame having transmitter coil arrays removably attached thereto to enable auto registration, as well as tracking of an instrument relative to the stereotactic head frame.

In one embodiment, a stereotactic navigation system for navigating an instrument to a target within a patient includes a stereotactic head frame and a tracking device. The stereotactic head frame defines a navigable patient space and is operable to be rigidly coupled to the patient and used to assist in guiding the instrument to the target site. The tracking device is removably coupled to the stereotactic head frame and operable to track the position of the instrument relative to the stereotactic head frame. The tracking device is further operable to be removed from the stereotactic head frame during imaging of the patient with the stereotactic head frame.

In another embodiment, a stereotactic navigation system for navigating an instrument to a target within a patient includes a stereotactic head frame, an imaging device, a tracking device, a controller and a display. The stereotactic head frame defines navigable patient space and is operable to be coupled to the patient and used to assist in guiding the instrument to the target. The imaging device is operable to capture image data of the navigable patient space and of the stereotactic head frame. The tracking device is removably coupled to the stereotactic head frame and is operable to track the position of the instrument relative to the stereotactic head frame. The controller is operable to receive image data from the imaging device and operable to identify the stereotactic head frame in the image data. The controller is further operable to automatically register the image data with the navigable patient space upon identifying the stereotactic head frame in the image data, while the display is operable to display the image data.

According to another embodiment, a method for performing image guided stereotactic navigation includes attaching a stereotactic head frame that defines navigable patient space on a patient, capturing image data of the navigable patient space with the attached stereotactic head frame, attaching a tracking device to the stereotactic head frame, and automatically registering image data with the navigable patient space.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is a perspective view of three transmitter coil arrays, each having unique attachment characteristics for attachment to the stereotactic frame of FIG. 3;

FIG. 5a illustrates a perspective view of an integrated DBS lead according to the teachings of the present invention;

FIG. 5b illustrates a perspective view of another DBS lead with a trackable cannula according to the teachings of the present invention;

DETAILED DESCRIPTION OF THE PREFERRED EMBODIMENTS

The following description of the embodiment(s) is merely exemplary in nature and is not intended to limit the invention, its application, or uses. Moreover, while the present invention is discussed in detail below with reference to delivering a deep brain stimulation (DBS) lead to the brain, the present method and apparatus for performing stereotactic surgery may be utilized for any type of neurological procedure or instrument, including biopsy needles, cannulas, catheters, implants, guide wires, needles, and stylets, and may also be used for delivery of electricity, drugs, genes or cells, as well as for ablation of vascular blockages or tumors or any other neurological intervention in the brain.

Figure 1:
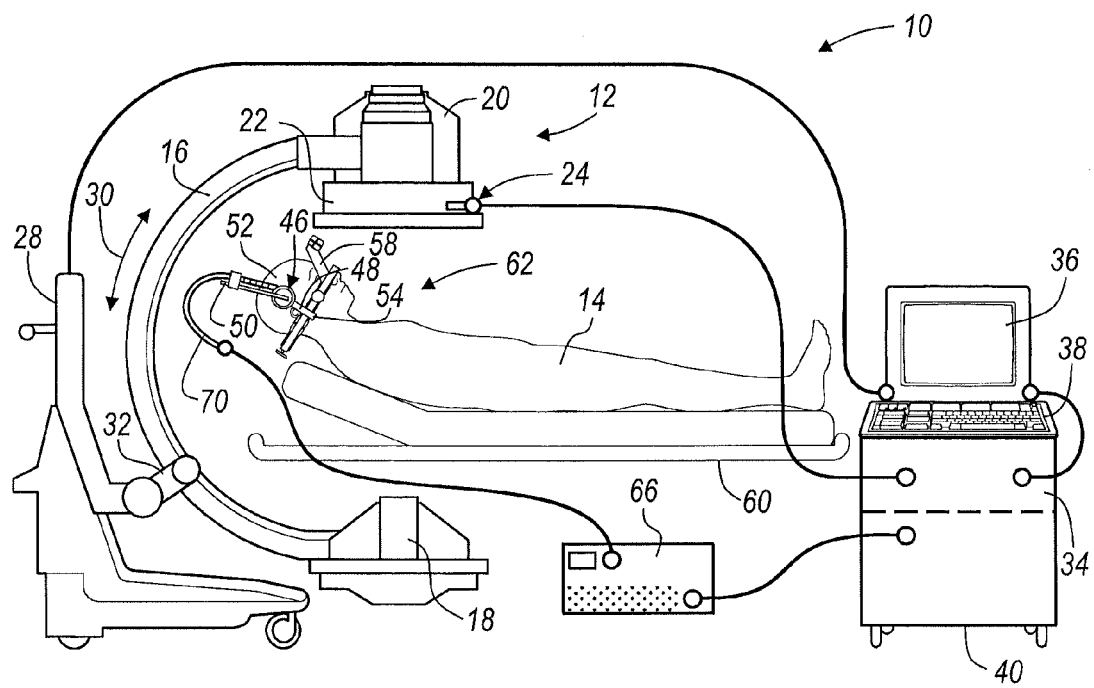
FIG. 1 is a diagram of a stereotactic navigation system for performing stereotactic surgery according to the teachings of the present invention.

FIG. 1 is a diagram illustrating an overview of a stereotactic image-guided navigation system 10 for use in performing stereotactic surgery. It should further be noted that the stereotactic navigation system 10 may be used to navigate any type of instrument or delivery system, including guide wires, needles, drug delivery systems, cell delivery systems, gene delivery systems, biopsy systems, DBS leads, micro electrodes, etc. Moreover, these instruments may be used for any type of neurological therapy or biopsy in the brain or be used to navigate or map the brain.

The stereotactic navigation system 10 may include an optional imaging device 12 that is used to acquire pre-operative or real-time images of a patient 14. In a typical stereotactic procedure, the patient 14 will have preoperative imaging, such as MRI imaging performed generally a few days before the surgical procedure to provide preoperative MRI image data for preoperative planning by a surgeon. The MRI imaging is typically performed without having a head frame attached to the patient 14 in order to reduce any patient discomfort. Once the preoperative MRI images have been taken, the surgeon will typically then plan the appropriate surgical procedure, based upon the acquired data.

Typically, on the day of surgery, the patient 14 is then imaged with a CT imaging device. The optional imaging device 12, can be any type of imaging device, such as a fluoroscopic x-ray imaging device or the CT imaging device. With CT imaging, the patient will have a series of CT scans taken on the area of interest for the stereotactic procedure. The patient will also typically be scanned with a head frame positioned on the patient 14, further discussed herein. The preoperative MRI image data may then be merged with the CT image data using known image fusion packages, as is known in the art.

For example, a point merge technique may be used where three points in the MRI image data and corresponding three points in the CT image data is identified by the surgeon or selected by the computer to do a point merge of the preoperative MRI data with the CT image data. Another exemplary auto image fusing system, is set forth in U.S. Ser. No. 09/733, 055, filed on Dec. 11, 2000, entitled "Method and Apparatus for Cross-Modality Image Registration", which is hereby incorporated by reference in its entirety. Other known image merging techniques may also be used, such as the use of fiducial markers. In this regard, distinct identifiable fiducial markers will be attached to the patient 14 during the preoperative MRI scan, so that they are identifiable in the MRI image data. These fiducial markers are not removed from the patient after the MRI image data has been captured and are thus also visible when the CT image data is captured, such that corresponding common points between the two sets of image data can be identified, thereby allowing for merging or fusion of the images, as is known in the art. Other types of known merging techniques include the use of surface contours or anatomical landmarks, which can be either manually or automatically identified by the system to provide another merge option.

As opposed to a CT imaging device 12, another exemplary imaging device 12 may be the use of a fluoroscopic x-ray imaging device that may be used in place of the CT imaging device or used in addition to the CT imaging device for later verification purposes, further discussed herein. In this regard, a similar image fusion between the preacquired image data and the later fluoroscopic x-ray imaging data can also be merged as discussed above.

If the imaging device 12 is a fluoroscopic x-ray imaging device 12 it may include a C-arm 16 having an x-ray source 18, an x-ray receiving section 20, an optional calibration and tracking target 22 and optional radiation sensors 24. The calibration and tracking target 22 includes calibration markers 26 (see FIGS. 2a-2b), further discussed herein. A C-arm controller 28 captures the x-ray images received at the receiving section 20 and stores the images for later use. The C-arm controller 28 may also control the rotation of the C-arm 16. For example, the C-arm 16 may move in the direction of arrow 30 or rotate about the long axis of the patient 14, allowing anterior or lateral views of the patient 14 to be imaged. Each of these movements involve rotation about a mechanical axis 32 of the C-arm 16. In this example, the long axis of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the fluoroscopic imaging device 12 generates x-rays from the x-ray source 18 that propagate through the patient 14 and calibration and/or tracking target 22, into the x-ray receiving section 20. The receiving section 20 generates an image representing the intensities of the received x-rays. Typically, the receiving section 20 includes an image intensifier that first converts the x-rays to visible light and a charge coupled device (CCD) video camera that converts the visible light into digital images. Receiving section 20 may also be a digital device that converts x-rays directly to digital images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used depending on the type of therapy performed. Alternatively, the imaging device 12 may only take a single image with the calibration and tracking target 22 in place. Thereafter, the calibration and tracking target 22 may be removed from the line-of-sight of the imaging device 12. Again, it should be noted that the imaging device 12 is optional and may be utilized during the stereotactic procedure to merely confirm that the instrument has hit the desired target or only used to merge the image data with the pre-operative MRI image data.

Two dimensional fluoroscopic images taken by the imaging device 12 are captured and stored in the C-arm controller 28. Multiple two-dimensional images taken by the imaging device 12 may also be captured and assembled to provide a larger view or image of a whole region of a patient 14, as opposed to being directed to only a smaller portion or region of the patient 14. For example, multiple image data of the patient's brain may be appended together to provide a full view or complete set of image data of the brain that can be later used. These images are then forwarded from the C-arm controller 28 to a controller, computer or work station 34 having a display 36 and a user interface 38. The work station 34 provides facilities for displaying on the display 36, saving, digitally manipulating, or printing a hard copy of the received images from both the imaging device 12 and from pre-operative scans, such as the preoperative MRI scans as discussed herein.

The user interface 38 may be a keyboard, mouse, touch pen, touch screen or other suitable device that allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images. When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 40, further discussed herein. Alternatively, a person or physician may manually indicate when the imaging device 12 is actively imaging or this function can be built into the x-ray source 18, x-ray receiving section 20, or the control computer 28.

Figure 2A:
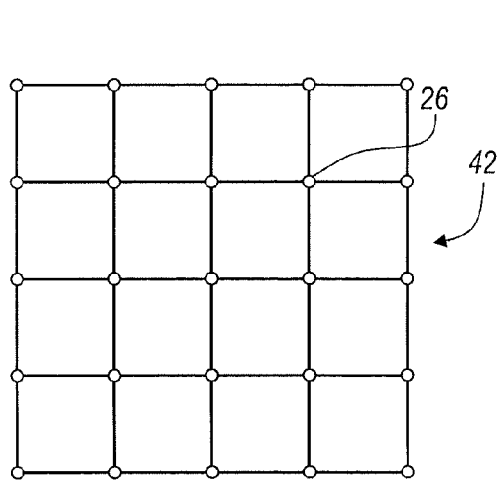
FIGS. 2a and 2b are diagrams representing undistorted and distorted views from a fluoroscopic imaging device.
Figure 2B:
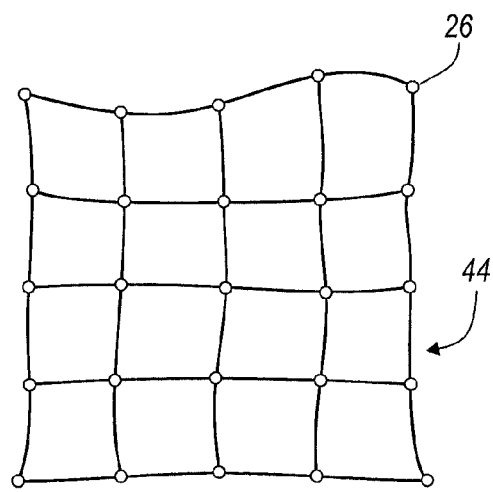

Fluoroscopic C-arm imaging devices 12 that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 42 of the checkerboard arranged calibration markers 26. The image taken by the receiving section 20, however, can suffer from distortion, as illustrated by the distorted calibration marker image 44, shown in FIG. 2b.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 42 (see FIG. 2a).

A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While a fluoroscopic imaging device 12 is shown in FIG. 1, any other alternative 2D, 3D or 4D imaging modality, as already discussed herein, may also be used for either or both preoperative and intraoperative imaging. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intra-vascular ultrasound (IVUS), ultrasound, intra-operative CT or MRI may also be used to acquire 2D, 3D or 4D pre-operative or real-time images or image data of the patient 14, further discussed herein. The images may also be obtained and displayed in two, three or four dimensions. In more advanced forms, four-dimensional surface rendering of the body may also be achieved by incorporating data from an atlas map or from pre-operative image data captured by MRI, CT, MSCT, HIFU, OCT, PET, etc. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, may also provide functional image data superimposed onto anatomical data to be used to confidently reach target sights within the areas of interest. It should further be noted that the fluoroscopic imaging device 12, as shown in FIG. 1, provides a virtual bi-plane image using a single-head C-arm fluoroscope 12 by simply rotating the C-arm 16 about at least two planes, which could be orthogonal planes to generate two-dimensional images that can be converted to three-dimensional volumetric images. By acquiring images in more than one plane, an icon representing the location of an instrument or lead, introduced and advanced in the patient 14, may be superimposed in more than one view on display 36 allowing simulated bi-plane or even multi-plane views, including two and three-dimensional views.

These types of imaging modalities may provide certain distinct benefits and disadvantages for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data generally requires registration and compensation for motion correction, further discussed herein.

Positron emission tomography (PET) imaging is generally a pre-operative imaging procedure that exposes the patient to some level of radiation to provide a 3D image. PET imaging provides functional information and also generally requires registration and motion correction.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction.

Ultrasound imaging is also generally an intra-operative procedure using a non-ioning field to provide either 2D, 3D, or 4D imaging, including anatomy and blood flow information. Ultrasound imaging provides automatic registration and generally does not need to account for any motion correction.

Regarding the use of atlas mapping, atlas maps may be utilized during the preplanning or preoperative stage to locate target sites within the brain of the patient 14 or any other region of interest. For example, these sites may include the basil ganglia, the sub-thalamic nucleus (STN) and various ventricles within the brain. In this regard, known neurological atlas maps may be used and scaled to the particular patient 14 or patient specific atlas maps may also be utilized that are updated over time. In this regard, over multiple procedures, enhancements and refinements in the location of certain desired sites within the neurological structure may be updated as these procedures are performed, thus providing an atlas map that is updated with each surgical procedure to provide more precise mapping by performing more procedures and gathering additional data. These neurological atlas or patient specific atlas maps may then be superimposed onto the pre-acquired images to identify relevant locations of interest. These patient specific atlases, sometimes referred to as iso-dose curves, provide the recommended target for the desired site and scale it to the actual patient 14 based on the historical data previously gathered. Examples of these systems are set forth in U.S. Pat. No. 6,009,212, entitled "Method And Apparatus For Image Registration", issued Dec. 28, 1999 and U.S. Pat. No. 6,226,418, entitled "Rapid Convolution Based Large Deformation Image Matching Via Landmark And Volume Imagery", issued May 1, 2001, each of which are hereby incorporated by reference.

The stereotactic navigation system 10 further includes a stereotactic frame or system 46 (see FIG. 3a), further discussed herein. An exemplary stereotactic frame is a stereotactic frame known as CRW, offered by Radionics, Inc., which may be utilized with the stereotactic navigation system 10. The stereotactic frame 46 is generally based on the center-of-arc principle and the basic components include a Cartesian coordinate head frame or ring 48 that defines a navigatable patient space area bounded within the area of the head frame 48, and a semi-circular trajectory arc 50, further discussed herein. The head frame 48 may be fixed to the patient's head 52, via pins 56. The head frame 48 also includes a variety of interchangeable front pieces 58 that are known in the art to provide various flexibility to access the patient's nose and mouth.

After the head frame 48 of the stereotactic frame 46 has been fixed to the head 52 of the patient 14, via fixation screws 56, the patient 14 will be preoperatively scanned using any type of imaging modality. These imaging modalities may again include CT, MRI, x-ray, PET, etc. The head frame 48 is designed to be compatible with all these types of imaging modalities, as is known in the art. Generally, preoperative or intraoperative CT and MRI scans are made parallel to the head frame 48. Once the patient 14 has been scanned with the head frame 48, and after pre-operative planning has been conducted, the patient 14 is positioned atop an OR table 60 and the semi-circular arc 50 is attached to the head frame 48. The center-of-arc principles of conventional stereotactic frames permits full flexibility in terms of access to all intracranial areas. This type of stereotactic frame also provides freedom of target choice and trajectory entry point selections. Posterior fossa transphenoidal and full lateral approaches are possible in addition to all other approaches utilizing the stereotactic system 46.

Examples of various types of procedures that may be performed using the stereotactic system 46 include diagnostic procedures related to the areas, such as tumors, systemic disorders and infectious diseases. Therapeutic processes may include intra-cavitary treatments, gamma knife surgery, implantations, evacuations, radioactive seeds and brachytherapy. The stereotactic system 46 may also be used for stereotactic microsurgery in relation to guidance, small lesions and foreign body removal. The stereotactic system 46 may also be employed to correct for movement disorders, pain, and epilepsy or any other ailment.

The stereotactic navigation system 10 further includes an electromagnetic navigation and tracking system 62. The electromagnetic navigation and tracking system 62 includes multiple transmitter coil arrays 64 each attached to the stereotactic system 46, the coil array controller 40, a navigation probe interface 66 and a plurality of electromagnetic sensors 68 coupled to an instrument 70, as well as to the stereotactic system 46, further discussed herein. It should further be noted that the entire tracking system 62 or parts of the tracking system 62 may be incorporated into the imaging device 12, including the work station 34 and radiation sensors 24. Incorporating the tracking system 62 will provide an integrated imaging and tracking system. Any combination of these components may also be incorporated into the imaging system 12, which again can include a fluoroscopic imaging device or any other appropriate imaging device used for preoperative and/or real-time intraoperative imaging.

Figure 3A:
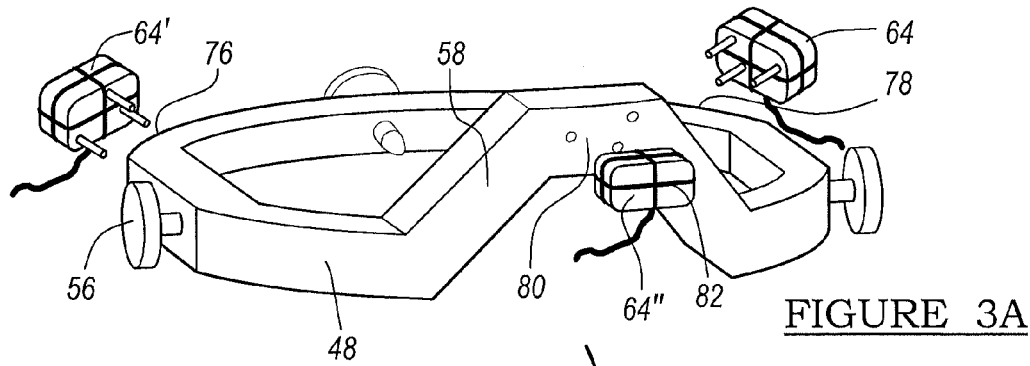
FIG. 3a is a perspective view of a stereotactic frame according to the teachings of the present invention.
Figure 3B:
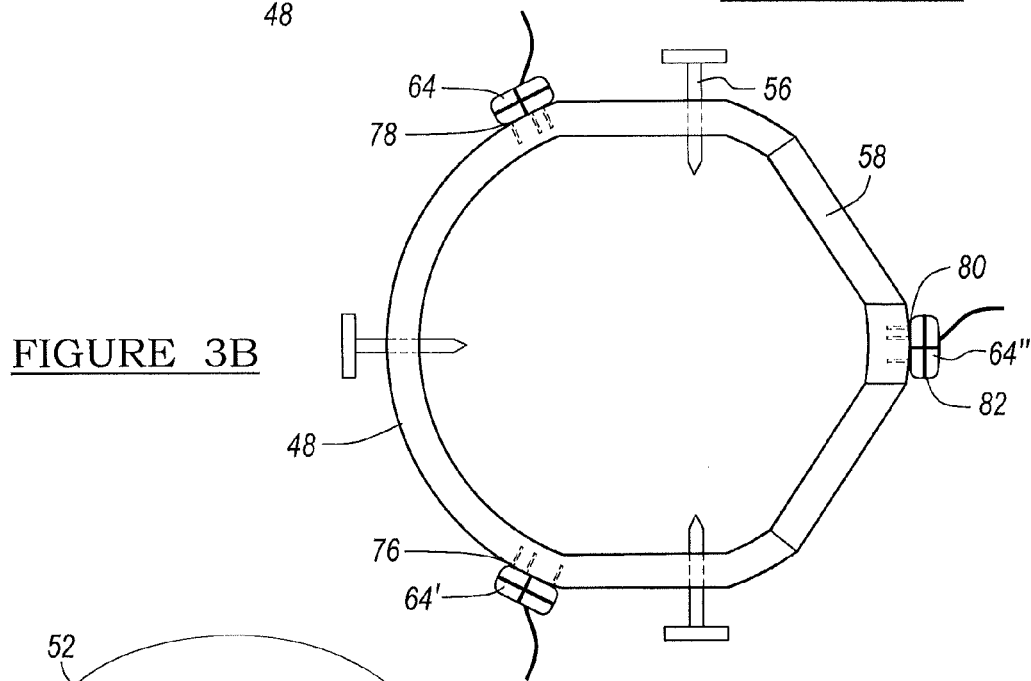
FIG. 3b is a top view of the stereotactic frame according to the teachings of the present invention.
Figure 3C:
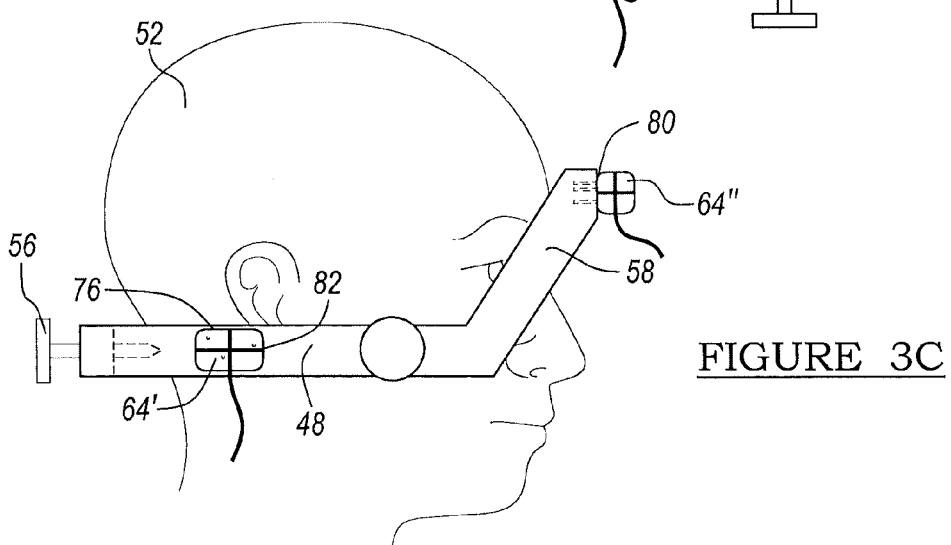
FIG. 3c is a side view of the stereotactic frame according to the teachings of the present invention.

As illustrated in FIGS. 3a-3c, the transmitter coil arrays 64 are shown attached to the stereotactic head frame 48. Three transmitter coil arrays 64 are shown positioned about the stereotactic frame 48 with the understanding that any appropriate number of coil arrays 64 may be used. The transmitter coil arrays 64 are removably attached to the stereotactic frame 48, via a removable attachment mechanism 72. The removable attachment mechanism 72 is illustrated in FIG. 4 as three dowels or rods extending from each transmitter coil array 64 with each set of dowels 74 having an unique pattern. Each unique pattern is designed to fit in only one unique hole pattern on the stereotactic frame 48. In this way, the first transmitter coil array 64 is located at position 76, the second transmitter coil array 64' is located at position 78 and the third transmitter coil array 64" is located at position 80. It will also be understood that any type of appropriate removable attachment mechanism may be employed. Moreover, it should be noted that each coil array 64 may be substantially identical with the attachment mechanism 72 being removably coupled to each transmitter coil array 64 where each attachment mechanism 72 has a unique shape or design to provide individual discreet locations for each coil array 64. In this way, common sensor arrays 64 having the same configurations may be provided and subsequently attached to the attachment mechanisms 72, each having a unique or keyed configuration for different locations.

Each transmitter coil array 64 is removable from the stereotactic frame 48 so that the patient 14 can be scanned preoperatively with an imaging device, such as CT or MRI without generating any distortion from the metallic components of the transmitter coil arrays 64. Also, since the removable attachment mechanism 72 for each transmitter coil array 64 has an unique attachment pattern, each transmitter coil array 64 can be repeatably affixed and removed from the head ring 48 in a prespecified factory calibrated method. It should also be pointed out that each transmitter coil array 64 is located at sites 76, 78 and 80, such that a substantially uniform and navigable electromagnetic field generated by the three transmitter coil arrays 64 will be within the center of the stereotactic space or navigable patient space bounded within the stereotactic frame 48, resulting in the highest level of accuracy being near the target. In other words, the transmitter coil arrays 64 are positioned to optimize the electromagnetic field in order to place this field along the trajectory path and target within the space bounded within the stereotactic frame 48.

Each transmitter coil array 64 may include a plurality of coils, such as three orthogonal coils 82 that are each operable to generate distinct electromagnetic fields into a navigation region within the stereotactic frame 48, which is sometimes referred to as patient space. Any other appropriate coil configuration may also be used. Representative electromagnetic systems, are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

It should also be pointed out that since each transmitter coil array is directly affixed to the head 54 of the patient 14, there is no need for a separate dynamic reference frame, which is typically required for conventional frameless stereotaxy. In other words, since the transmitter coil arrays 64 are attached directly to the head 54 of the patient 14 via the head frame 48, any movement of the patient's head 54 will be detected, thereby eliminating the need for a dynamic reference frame. This may also eliminate any errors that are associated with use of dynamic referencing. Moreover, this provides for automatic registration between the patient space and image space, further discussed herein. Additionally, the most accurate readings will be optimally near the target or therapy site by providing a uniform electromagnetic field within the area bounded by the stereotactic frame 48, thereby further enhancing the accuracy of lead or instrument placement. Finally, since the fixation points for the transmitter coil array 64 are repeatable, the computer work station 34 may continuously check to make sure that the stereotactic frame 48 has not been bent or warped, since the navigation system 62 will know precisely where each transmitter coil array 64 should be positioned in relation to the other transmitter coil arrays 64' and 64".

Each transmitter coil array 64 is controlled or driven by the coil array controller 40, via either a wire connection as shown or via a wireless connection using technology known in the art. The coil array controller 40 may drive each coil 82 in each transmitter coil array 64 in a time division multiplex or a frequency division multiplex manner. In this regard, each coil 82 may be driven separately at a distinct time or all of the coils 82 may be driven simultaneously with each being driven by a different frequency. Upon driving each coil 82 in each transmitter coil array 64, with the coil array controller 40, electromagnetic fields are generated within the area bounded by the stereotactic frame 48, which is again sometimes referred to as the patient space. The electromagnetic field that is generated in the patient space induces currents in the electromagnetic sensors 68 that are positioned on the lead 70, as well as positioned on the stereotactic frame 48 and arc 50, further discussed herein. These induced signals from the electromagnetic sensors 68 are delivered to the navigation probe interface 66, again either via a wire or wireless connection, and subsequently forwarded to the coil array controller 40. The navigation probe interface 66 provides all the necessary electrical isolation for the stereotactic navigation system 10. The navigation probe interface 66 also includes amplifiers, filters, and buffers required to directly interface with the sensors 68.

Turning to FIG. 5*a*, a representative integrated DBS lead 70 is illustrated. DBS lead 70 includes an internal substantially rigid stylet 84 that is wrapped in a plastic compound and includes multiple external contacts 85 embedded along the distal end of the lead 70. The contacts 85 are tied to a remote pulse or electrical generator and are used to deliver a small amount of electric current to locations defined between the spaces of the contacts 85. Thus, DBS lead 70 is essentially a method for delivering electricity to the brain similar to a pacemaker for a heart. The current is used for various types of treatment of the brain, as is known in the art. Also embedded within the lead 70 and wrapped around the stylet is at least one or multiple electromagnetic sensors or coils 68, which are utilized to track the location of the lead 70 as it is positioned, via the stereotactic system 46. With the use of the electromagnetic sensors 68, the location of the lead 70 relative to the patient's anatomy is known without the need for any real-time or post-operative imaging, such as fluoroscopic imaging, thereby eliminating the need for the imaging device 12, if desired. The lead 70 may also include multiple EM sensors 68 to provide a more accurate location and position of the sensor relative to the preacquired images. For example, each electromagnetic sensor 68 may be positioned with each contact 85 so that the precise location of each contact 85 can be tracked. The multiple EM sensors 68 are generally fixed to the stylet 84 and spaced axially from one another along the distal end of the lead 70 similar to the contacts 85. By providing multiple sensors 68, any bending of the DBS lead 70 can be detected. The EM sensors 68 are again formed as electromagnetic receiver coils, such that the electromagnetic field generated by the transmitter coil arrays 64 induces current in the electromagnetic receiver coils 68. The lead 70 may also include one or more sensors, which are operable to sense various physiological signals. The lead 70 may also be provided with an open lumen, to allow for delivery of a medical device, pharmaceutical agents, cells or genes.

In an alternate embodiment, the electromagnetic sources or generators may be located within the integrated DB lead 70 and one of more receiver coils may be provided external to the patient 14 forming a receiver coil array similar to the transmitter coil arrays 64. In this regard, the EM sensors 68 will generate electromagnetic fields, which would be received by the coils 82 in the transmitter coil arrays 64. However, it should also be pointed out that any other type of tracking or localization sensors or systems may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. Other types of tracking systems include optical, acoustic, electrical field, RF, fiberoptic, and accelerometers. Accelerometers enable both dynamic sensing due to motion and static sensing due to gravity. An additional representative alternative localization tracking system, is set forth in U.S. Pat. No. 5,983,126, entitled "Catheter Location System and Method", issued Nov. 9, 1999, which is hereby incorporated by reference. The tracking systems may also include hybrid systems, which include portions of electromagnetic or optical or any combination thereof.

Turning now to FIG. 5*b*, a cannula or tube 87 having electromagnetic sensor 68 is illustrated. The tube 87 is cannulated throughout its length and is operable to pass or deliver a micro electrode and a later inserted lead 89 having a distal tip 91. The lead 89 also delivers electricity to the brain similar to the contacts 85 of the DBS lead 70, illustrated in FIG. 5*a*. In this regard, the tip 91 of the lead 89 is operable to deliver current to the brain at the desired target location, via an electrical generator 93, coupled to the lead 91 by way of transmission line 95. Since the electromagnetic sensor 68 is located at the distal end of the cannula or tube 87, the relative position or location of the lead 89 is known and since the lead 91 has a fixed length, the depth of the lead 89 is also determinable by knowing how far the lead 89 is extended through the cannula 87 by monitoring the length at the proximal end. The lead 89 generally will not include a sensor 68 since the lead 89 is very small in size and is generally not capable of supporting the sensor 68 directly. Again, it should also be noted that the cannula or tube 87 may also include multiple sensors 68 positioned along the cannula 87 similar to that shown in FIG. 5*a*.

Figure 6A:
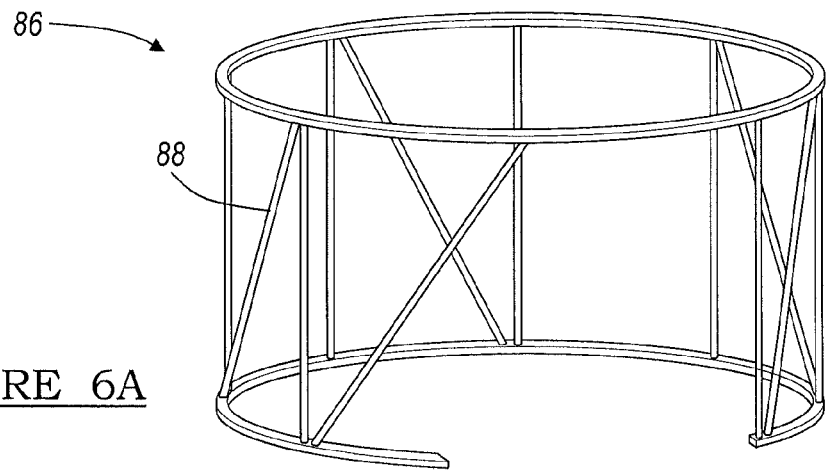
FIG. 6a is a perspective view of a fiducial head cage according to the teachings of the present invention.
Figure 6B:
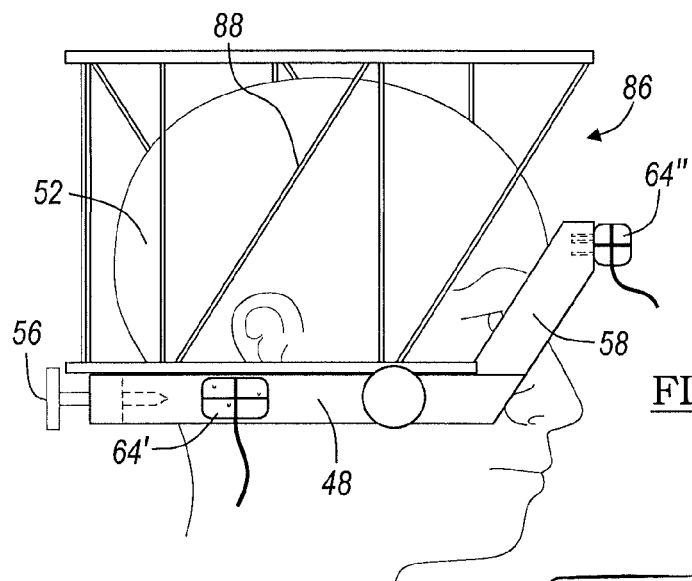
FIG. 6b is an assembled view of the fiducial head cage affixed to the stereotactic frame of FIG. 3.

Referring now to FIG. 6*a*, an optional fiducial head cage 86 is illustrated. The fiducial head cage 86 includes multiple radio opaque marking rods or other radio opaque-shaped markers 88 mounted throughout the head cage 86 to substantially fill the volume about the head cage 86. The fiducial head cage 86 snaps on to the stereotactic frame 48 in a predetermined location, as shown in FIG. 6*b*, prior to preoperative imaging. Again, the patient 14 may be scanned with the fiducial cage 86 attached to the stereotactic frame 48 and with the transmitter coil arrays 64 removed to eliminate any interference during the imaging using CT, MRI, etc. Alternatively, the patient 14 may be scanned with only the head frame 48.

Figure 6C:
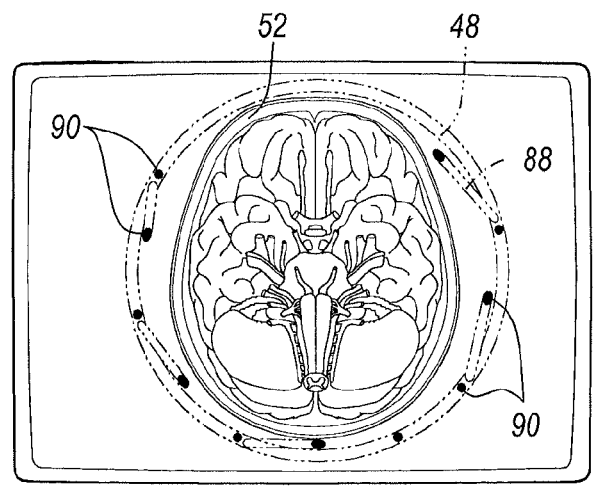
FIG. 6c is a scanned image of the fiducial head cage of FIGS. 6a and 6b.

Referring now to FIG. 6*c*, a representative scan of the patient 14 is illustrated that identifies the radio opaque marking rods 88 attached to the fiducial head cage 86. Since the rods 88 are radio opaque, they show up well as circles 90 in the scanned image, which in this example, is an axial MR slice. Since the fiducial rods 88 are fixed at known locations or positions, and at known angels, the work station 34 can automatically identify these fiducial circles 90 in each slice and acquire a mapping between a point on the anatomy and its location relative to the fixed stereotactic frame 48 in the image data. This enables automatic registration between the preacquired image data and patient space. In other words, since each transmitter coil array 64 is repeatably fixable on the head frame 48, the work station 34 can establish the spatial relationship between the transmitter coil arrays 64 and any point on the patient 14. As a result of this relationship, whenever an EM sensor 68 is brought into the electromagnetic field of the patient space, its spatial relationship relative to the transmitter coil arrays 64 is translated to a spatial relationship with the patient anatomy. Thus, since the rods 88 are at known positions and known angles, by identifying the rods 88 inside the image data, this creates a 3D data set and by knowing the initial positions and angles, this allows the work station 34 to perform an automatic registration between the preacquired image scan and patient space. Moreover, since the fiducial rods 88 are positioned to cover more volume in the area of interest, it is a very accurate registration technique.

Alternatively, or in combination, the other auto registration technique involves the use of the distinct or unique hole patterns or fiducial marks positioned in the stereotactic frame 48, which receives the dowels 74 of the removable attachment mechanism 72. In this regard, since the stereotactic frame 48 is positioned on the patient 14 during the initial image scanning, the unique hole patterns at each site 76, 78, and 80 may be identified by the work station 34 using known pattern recognition algorithms. Since these hole patterns are at a known location where each transmitter coil array 64 is located, the work station 34 may perform auto registration, by identifying each unique hole pattern. In other words, since the stereotactic frame 48 is rigidly fixed to the patient 14, and does not move between the pre-scanning and the surgical procedure, by identifying the location of the unique hole patterns and by knowing where each transmitter coil array 64 is located after scanning enables the work station 34 to calculate a translation between the three-dimensional image data and patient space, as is known in the art to enable auto registration.

Again, it should be noted that the attachment mechanisms 72 may be any other removable attachment mechanism that is able to uniquely attach each individual transmitter coil array 64 to the stereotactic frame 48. Moreover, the work station 34 may be able to identify other unique features other than hole patterns depending on the removable attachment mechanism utilized to perform the auto registration technique. Finally, it should also be pointed out that since auto registration may be performed with simply using the stereotactic frame 48, the fiducial head cage 86 is an optional procedure to provide further enhanced accuracy since it covers more volume in the area of interest.

Figure 7A:
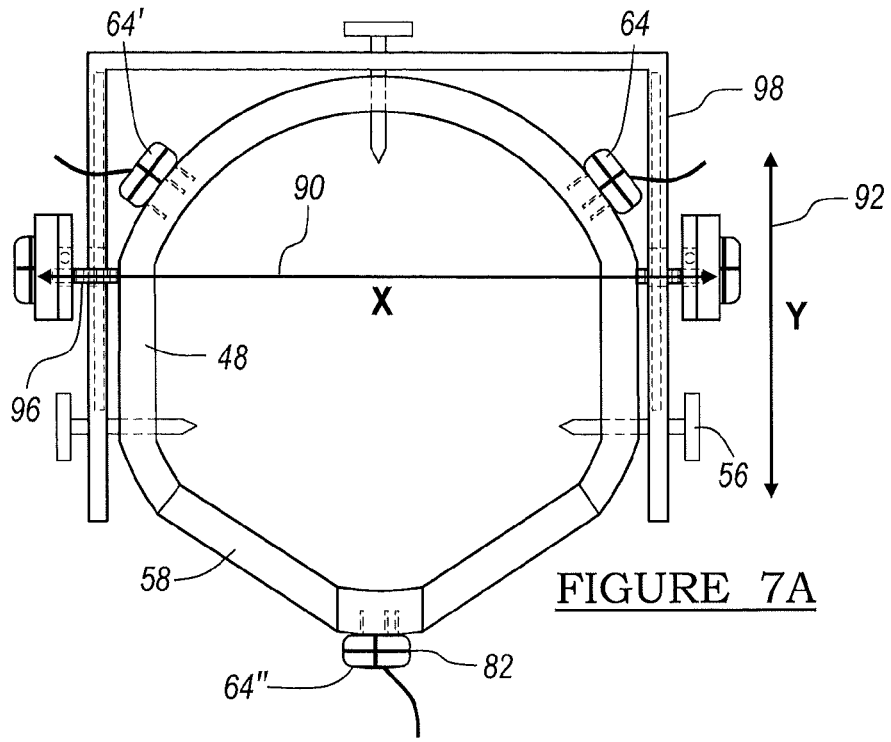
FIG. 7a is a top view illustrating the adjustment of the stereotactic frame in the x and y directions.
Figure 7B:
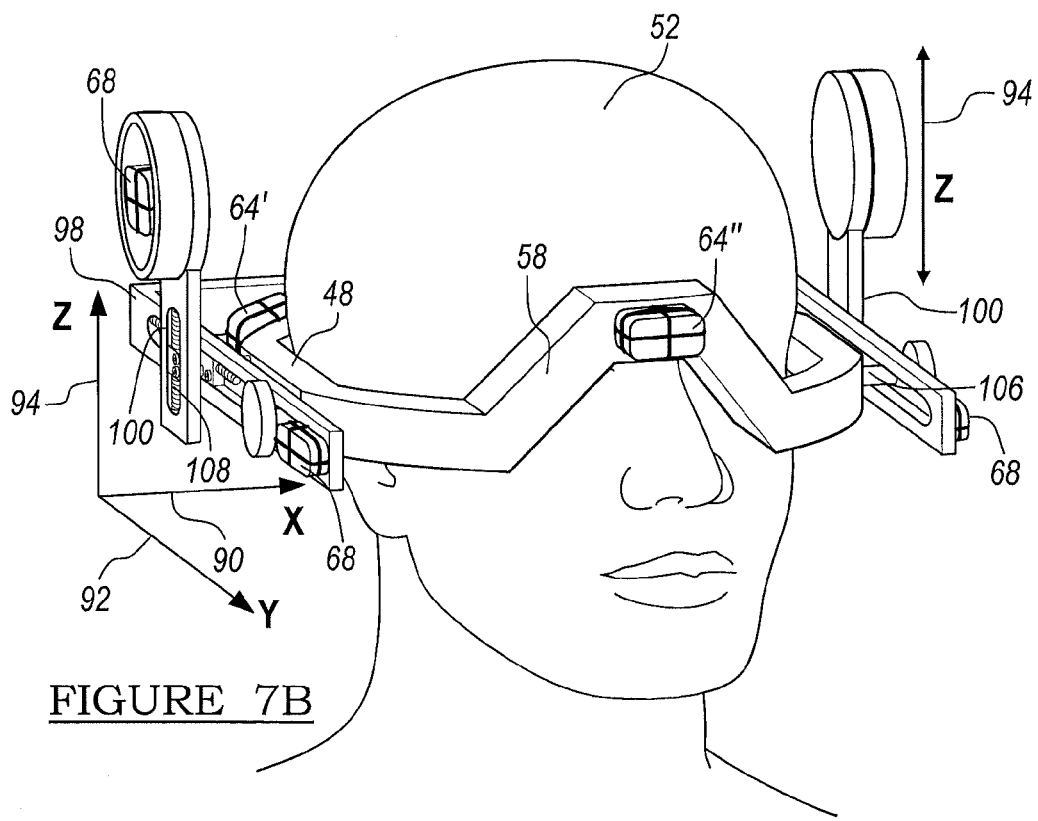
FIG. 7b illustrates the adjustment of the stereotactic frame in the z direction.

Referring now to FIGS. 7a and 7b, adjustment of the stereotactic frame 48 in the Cartesian coordinate system (x, y, and z axes) is illustrated. In this regard, the target site in which the lead 70 or other instrument is delivered to is generally located within the centroid of the stereotactic frame 48. Thus, in order to adjust this target site to any location within the head 52 of the patient 14, the stereotactic frame 48 is movable about an x-axis 90, a y-axis 92, and a z-axis 94 using conventional x, y, and z stereotactic frame stages or any other appropriate adjustment mechanism. By adjusting the stereotactic frame 48 about the x-axis 90, y-axis 92, and z-axis 94, the corresponding target site, which is generally located within the centroid of the stereotactic frame 48 is correspondingly adjusted.

The stereotactic frame 48 is movable along the x-axis 90 via an x-stage 96, movable along the y-axis 92, via a y-stage 98, and movable along the z-axis 94, via a z-stage 100. Because the x, y, and z-stages 96, 98, and 100 are located and adjusted in space using the electromagnetic tracking system 62, further discussed herein, the stereotactic navigation system 10 substantially reduces or eliminates errors associated with manual adjustable granularity scales used on conventional stereotactic frames. Moreover, the x, y, and z adjustments are also not limited by the grandularity of the scales. Still further, since the x, y, and z-stages 96, 98, and 100 are monitored via the navigation system 62, the work station 34 can monitor to make sure that the x, y, and z-stages 96, 98, and 100 are aligned orthogonally. Further, since the x, y, and z-stages 96, 98, and 100 are adjustable, the surgeon is able to retain the ability to adjust the stages, so that the anatomical target or site is at the center of the stereotactic frame 48 regardless of the entry or trajectory point, further discussed herein.

Figure 8A:
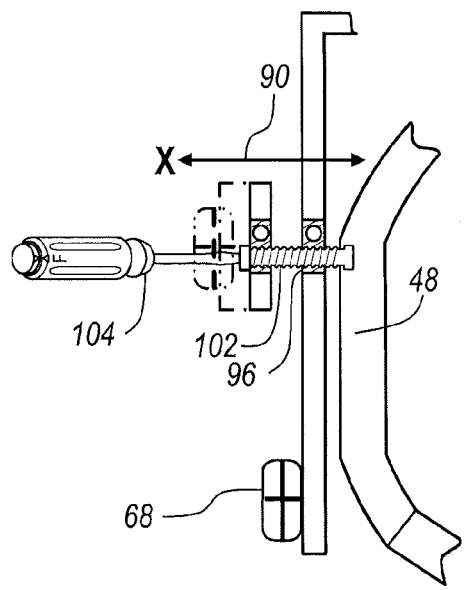
FIG. 8a illustrates a x-adjustment stage along with an adjustment screw driver.
Figure 8C:
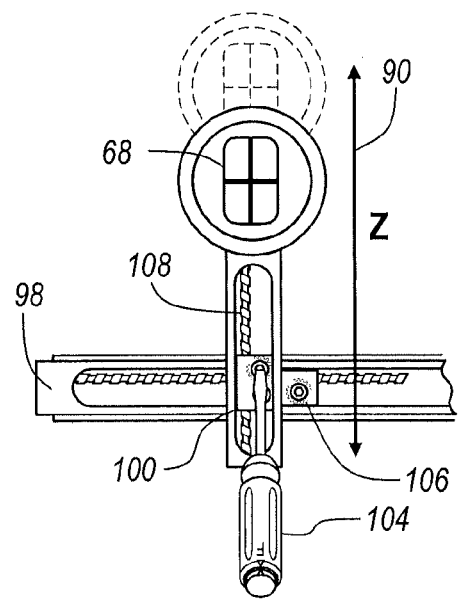
FIG. 8c illustrates a z-adjustment stage along with the adjustment screw driver.
Figure 8B:
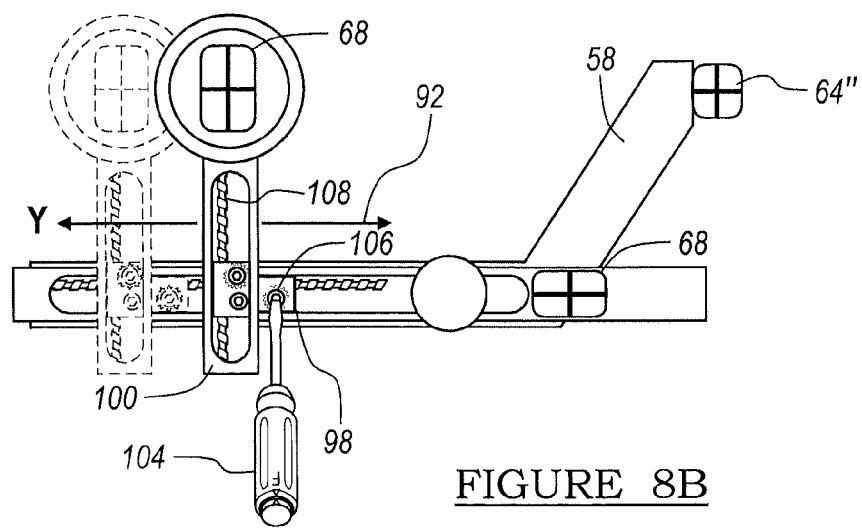
FIG. 8b illustrates a y-adjustment stage along with the adjustment screw driver.

Referring now to FIGS. 8a-8c, one exemplary adjustment system is illustrated with the understanding that any other adjustment configurations may also be employed with the stereotactic navigation system 10. Referring specifically to FIG. 8a, the x-stage 96 is illustrated. The x-stage 96 is adjusted via a screw and worm gear 102, which is operable to be driven by an automated screw driver 104. In this regard, the screw driver 104 may be battery powered or directly powered, via the navigation probe interface 66. The screw driver 104 includes two gear settings, a high gear setting for coarse adjustments, and a low gear setting for very fine, sub-millimeter adjustments. In this way, the physician or user will initially set the gearing to a high setting to adjust the x-stage 96 very near the desired location, and switch the gear setting to a low setting and perform the fine adjustment to reach the adjustment along the x-axis 90. Coupled to the x-stage 96 is an electromagnetic sensor 68 that moves with the stage 96 to enable the electromagnetic tracking system 62 to detect the accurate position or location of the x-stage 96 automatically. It should also be pointed out that the adjustment can be a closed loop adjustment, such that the screw driver is controlled via the work station 34 and will automatically stop when the x-stage 96 reaches its appropriate location, further discussed herein. Moreover, any other type of adjustment mechanism may be utilized, such as a robotic mechanism that completely automates the adjustment of the x-stage 96, as well as the other stages involved. In this regard, the work station 34 again can automatically adjust the stage and monitor the real-time location, via the EM sensor 68 attached to each stage, thereby providing a completely automated closed loop feedback system for stage and target adjustment.

Turning to FIG. 8b, the y-adjustment stage 98 is illustrated, which is similar to the x-adjustment stage. The y-adjustment stage 98 also includes a screw and worm gear 106, which is driven by the screwdriver 104. Additionally, the y-stage 98 further includes an electromagnetic sensor 68 also used to provide location information for the y-stage, similar to the x-stage 96.

Referring to FIG. 8c, the z-adjustment stage 100 is illustrated also having a screw and worm drive 108, which is driven by the screwdriver 104. Attached to the y-stage 100 is another EM sensor 68, which is comprised of either a single electromagnetic coil or multiple electromagnetic coils to provide a further level of accuracy.

Figure 9:
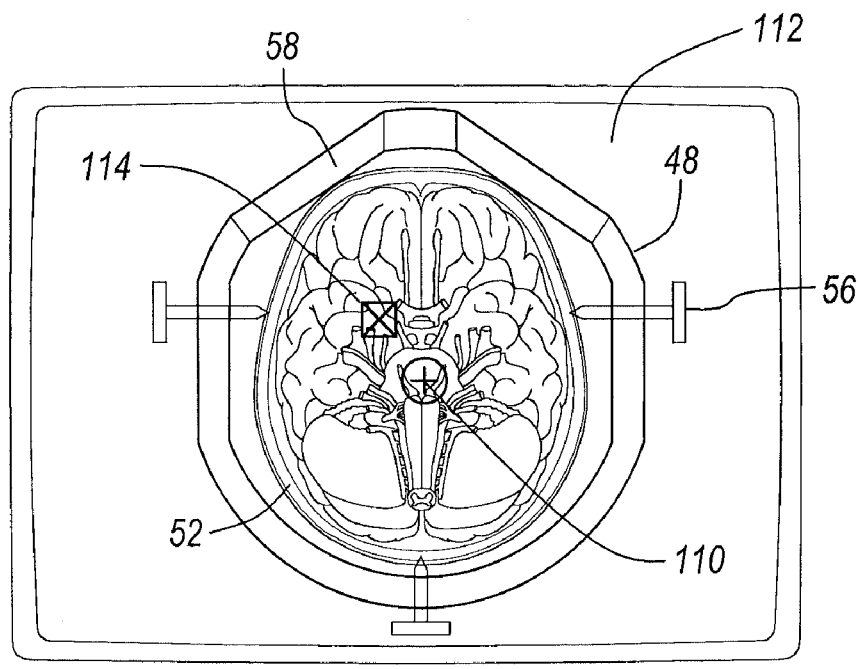
FIG. 9 illustrates a scanned image of a patient's brain identifying a desired target and the stereotactic frame centroid.

Turning now to FIG. 9, use of the stereotactic navigation system 10 to coordinate a target at the center of the stereotactic frame 48 is illustrated. In this regard, based upon preacquired imaging, such as CT or MRI imaging, a scan 112 of the patient's head 52 is illustrated in FIG. 9. This scan 112 also includes and captures an image of the stereotactic frame 48. As illustrated in FIG. 9, the standard centroid for the stereotactic frame is identified by reference numeral 110. Upon review of the scan 112, the surgeon will select a desired site or target 114 in which delivery of a surgical instrument or lead is desired. The target 114 is selected based upon the surgeon's preoperative planning and review of the preacquired image scans. Alternatively, atlas maps may be employed to determine or identify the target 114 and also used to determine the coordinates in which to adjust the head frame 48. Atlas information may also be used to direct the work station 34 to automatically adjust the head frame 48 location. Additionally, preacquired images can be merged with atlas images to also assist in identifying the desired target 114 which can be automatically identified by the work station 34.

The work station 34 is preloaded with the geometry of the stereotactic frame 48 and knows the location of the x, y, and z-stages 96, 98, and 100, via the electromagnetic tracking system 62. The work station 34 also knows the relationship of the anatomy to the stereotactic frame 48, as well as where the stereotactic frame 48 centroid 110 lies on the patient anatomy. Since the electromagnetic tracking system 62 tracks the x, y, and z-stages 96, 98, and 100, the work station 34 can direct the surgeon on how to adjust the x, y, and z-stages 96, 98, and 100 to make the centroid 110 of the stereotactic frame 48 align with the desired target 114. Here again, the work station can also automatically adjust the x, y, and z-stages 96, 98, and 100 in order to align the desired target 114 with the centroid 110 of the stereotactic frame 48 using known robotically-controlled mechanisms such as stepper motors.

Figure 10:
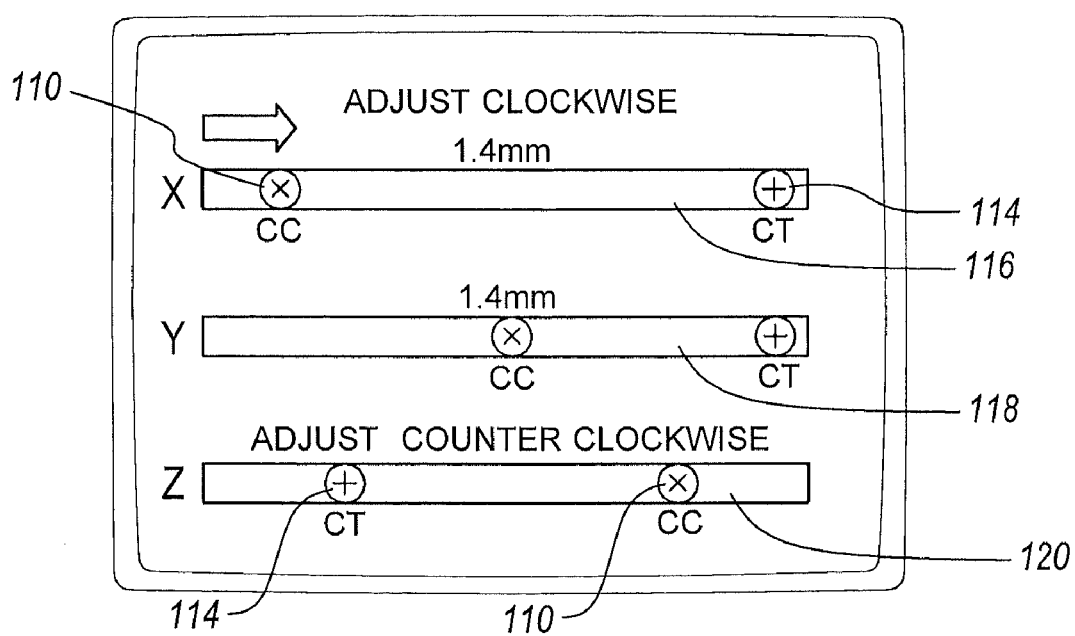
FIG. 10 illustrates a computer screen display identifying the adjustment along the x, y, and z-axes.

Referring to FIG. 10, an example of the display 36 illustrating adjustment scales for adjusting the x, y, and z-stages 96, 98, and 100 is illustrated. In this regard, an x-adjustment scale 116 identifies the current centroid 110 and the chosen target 114, along the x-axis 90. Likewise, a y-adjustment scale 118 and a z-adjustment scale 120 also illustrate the current centroid 110 relative to the chosen target 114 and relative to their corresponding axes. In order to align the centroid 110 of the stereotactic frame 48 on the chosen target or site 114, the surgeon will simply align the "x" with the "+" on each scale 116, 118, and 120 by adjusting the corresponding x, y, and z-stages 96, 98, and 100. Once the current centroid 110 aligns with the chosen target 114 along the x-axis 90, the y-axis 92, and the z-axis 94, the instrument, lead, or delivery device will hit the target 114 regardless of the trajectory entry point. Again, these adjustments along the x, y, and z-stages 96, 98, and 100 may be performed utilizing the battery driven screw driver 104, may be manually adjusted, via knobs, or can be fully robotically automated and driven, such as by stepper motors, via the work station 34 with a closed loop feedback path provided by the EM sensors 68 associated with each x, y, and z-stage 96, 98, and 100. By reviewing the scales 116, 118, and 120, simultaneous real-time feedback is visually provided to the surgeon, thereby assuring proper stereotactic frame 48 placement relative to the target 114.

The benefits of this system over conventional stereotactic frames is significant. In this regard, the target 114 once aligned with the centroid 110 places the most accurate electromagnetic field at the optimum location of the centroid 110 of the stereotactic frame 48, providing optimized accuracy. The stereotactic navigation system 10 also continuously verifies that the target 114 and the centroid 110 line up or that the relationship is maintained, via the work station 34 and the real-time feedback, via EM sensors 68. Moreover, an interoperative change in trajectory to reach the target 114 does not change or require target adjustment, via the x, y, and z-stages 96, 98, and 100, which makes preoperatively and intraoperatively preparation and planning easier and more efficient. The stereotactic navigation system 10 also does not require the physician or user to know the geometry of the stereotactic system 46 because the physician simply identifies the target 114 using a pointer probe or other device 38 or the work station 34 automatically identifies the target 114 based upon pre-programmed parameters. The x, y, and z-stages 96, 98, and 100 are then either manually or automatically adjusted to the computer generated set points, which appear on the x, y, and z scales 116, 118, and 120. Thus, once the target is selected, via the pointer probe 38 or any other input device, the work station 34 automatically provides the current location of each x, y, and z-stage 96, 98, and 100 relative to the chosen target 114, via the x, y, and z scales 116, 118, and 120. Additionally, the work station 34 may be configured to inhibit operation if the target 114 does not match the centroid 110. Upon matching the desired target 114 with the centroid 110 of the stereotactic frame 48, the work station 34 can provide an audible or visual indication that the setting has been reached, thereby initiating the surgeon to continue with the procedure.

Figure 11:
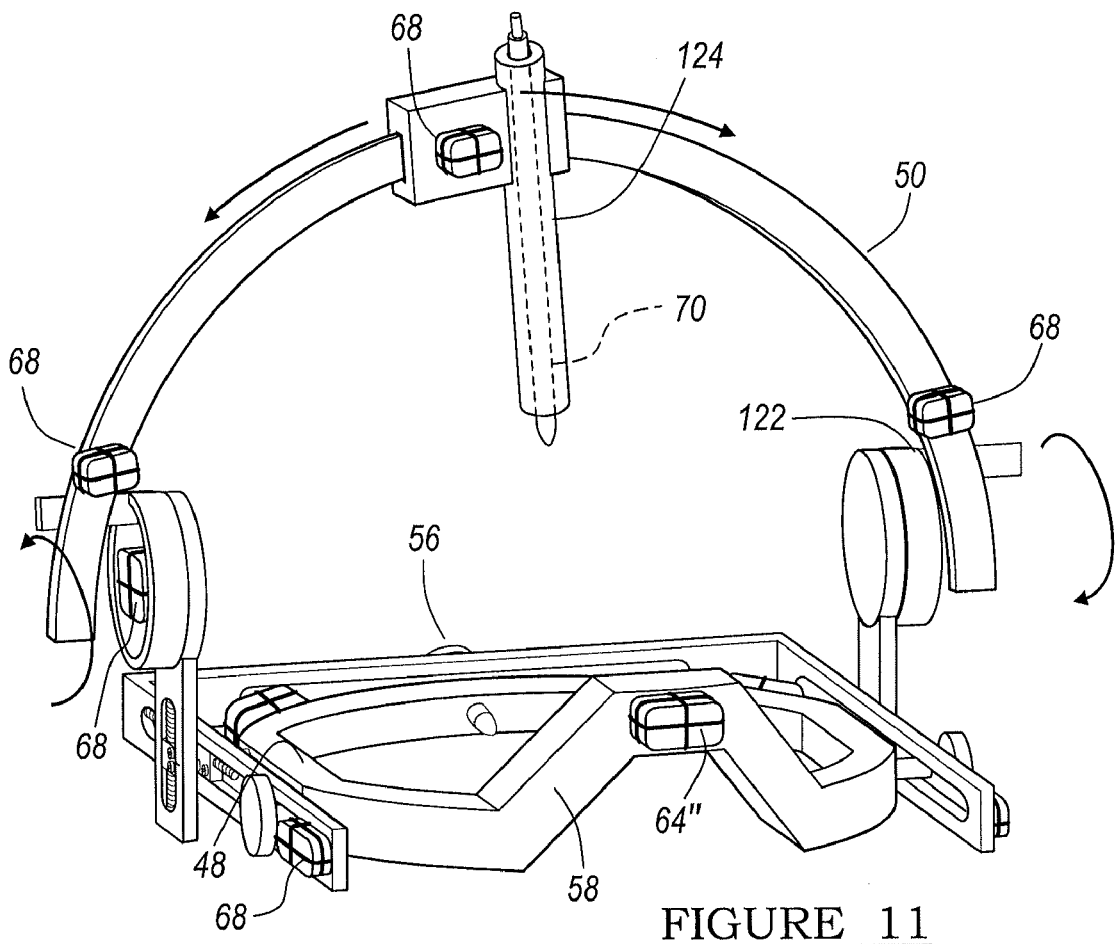
FIG. 11 illustrates a perspective view of the stereotactic frame with a movable trajectory guide according to the teachings of the present invention.
Figure 12:
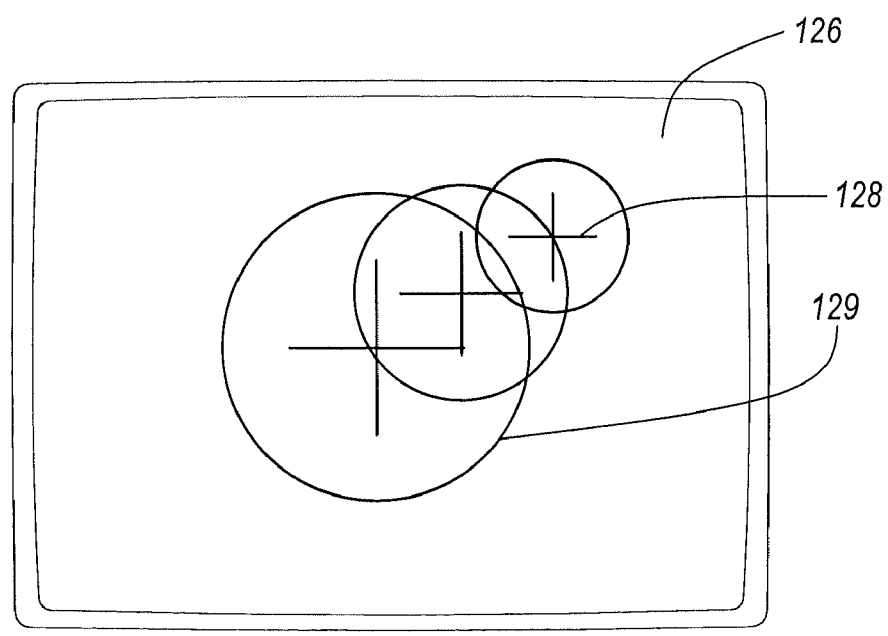
FIG. 12 illustrates a computer screen display of the mapped trajectory.

Referring now to FIGS. 11 and 12, use of the tool arc 50, which is attached to the stereotactic frame 48 is discussed in further detail. The arc 50 is movably coupled to the stereotactic frame 48 and is used to deliver a lead 70 or any other instrumentation or delivery system to the target 114. The arc 50 enables the trajectory of the lead 70 to be adjusted upon pivoting the arc 50 about pivot points 122, as well as by sliding a guide tube or tool holder 124 approximately 180° along the arc 50. Regardless of the trajectory selected, the lead 70 or instrument will always reach the target 114 by employing the center-of arc principle of the arc 50. In order to track the trajectory, as well as display it, as illustrated on screen 126 in FIG. 12, the arc 50 includes multiple EM sensors 68. In this regard, a pair of EM sensors 68 are attached to the distal ends of the arc 50 near the pivot points 122 and an EM sensor 68 is attached to the guide tube 124. In this way, pivoting about pivot points 122, as well as angular location about the arc 50 are monitored, via the EM sensor 68 and the electromagnetic tracking system 62.

Similar to the stage adjustments, the trajectory adjustments can be pre-planned and intraoperatively changed while at the same time providing simultaneous real-time feedback of the location and direction of the trajectory via display 126, illustrated in FIG. 12. In other words, the target 114 defines the x, y, and z adjustment of the stereotactic frame 48 and an entry point 128 defines where the arc 50 and guide tube 124 are. For a given target 114 and a given entry point 128, there can only be one set of x, y, and z adjustments and only one arc and guide tube combination. Similar to the x, y, and z adjustment, the work station 34 can identify whether to swing the arc 50 backward or forward and whether to swing the tool guide or tube 124 to the left or right. Once the desired trajectory has been reached, the work station 34 can provide either an audible or visual signal identifying that the proper entry point 128 has been set. Based upon the linear path along the tracked trajectory guide or arc 50, the actual lead trajectory can be calculated on the fly, and adjustments made intraoperatively until the actual trajectory matches the planned trajectory with the feedback given by the work station 34 and display 36, such as illustrated on the screen 126.

As illustrated in screen 126, a plurality of rings or circles 129 are illustrated representing the desired entry point 128 and the current trajectory of the lead 70 to the target 114. In other words, the circles 129 represent the axis of the lead 70 or instrument, such that when the axis of the lead 70 is directly over the desired entry point 128, the circles 129 are positioned concentrically, such that you are essentially looking directly down at the target 114 over the desired entry point 128. Upon positioning the rings 129 concentrically about the desired entry point 128, the desired trajectory is aligned with the actual trajectory similar to adjustment of the stages illustrated in FIG. 10. Other types of displays that provide 6-degree of freedom information may also be utilized, such as the display set forth in U.S. Ser. No. 10/354,562, entitled "Six Degree Of Freedom Alignment Display For Medical Procedures," filed Jan. 30, 2003, which is hereby incorporated by reference. Thus, the work station 34 provides real-time feedback on the adjustment of the actual trajectory to the desired trajectory or entry point 128. Again, real-time tracking eliminates the use of manually performing calculations and manually adjusting the frame 48 and arc 50, thereby significantly reducing the possibility of operator error. The EM sensors or coils 68 may also be continuously monitored, via the electromagnetic navigation system 62 to further monitor the geometry of the stereotactic frame 48 and the arc 50, thus alerting the user or surgeon if either become damaged or warped during the procedure. A dynamic representation of the trajectory can also be visualized relative to the points of anatomical interest. This saves time associated with choosing hypothetical entry points on the image and recalculating these points every time the entry point changes. This may also minimize minor trajectory errors associated with drilling the burr hole slightly off from the pre-planned site.

Figure 13:
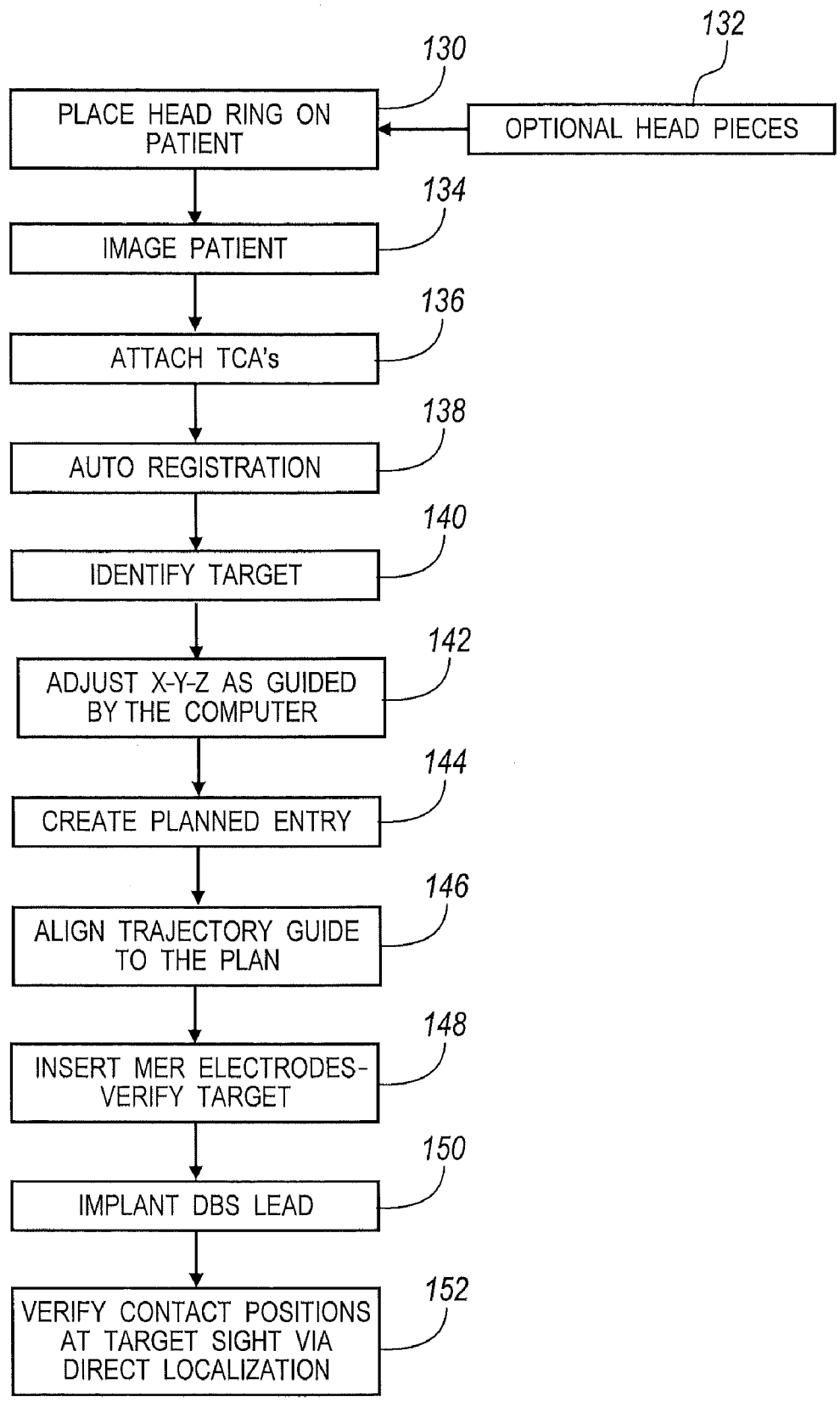
FIG. 13 is a logic block diagram illustrating a method for performing the stereotactic procedure according to the teachings of the present invention.

Turning finally to FIG. 13, a logic block diagram illustrating a method for utilizing the stereotactic navigation system 10 that employs the navigable stereotactic system 46 is illustrated in further detail. The procedure begins at block 130 where the stereotactic frame or head ring 48 is positioned on the patient 14. In addition to positioning the stereotactic frame 48 on the patient at block 130, the optional fiducial head cage 86 may also be attached to the stereotactic frame 48 at block 132. Once a stereotactic frame or head ring 48 is positioned on the patient 14, the procedure proceeds to block 134 where the patient is imaged with the stereotactic frame 48 and possibly the optional fiducial head cage 86. The patient 14 may be imaged using any type of imaging device, such as CT or MRI, since the stereotactic frame 48 is compatible all types of imaging modalities.

The CT and MRI scans are generally made parallel to the stereotactic frame 48, thereby providing maximum reproducibility and enabling the scans to be compared with each other and to atlas maps. In this regard, neurological procedures generally utilize a coordinate system based on two landmarks in the brain known in the art as the anterior commissure (AC) and posterior commissure (PC), such that the center of the brain is cut in half along the sagittal plane into left and right hemispheres. The x, y, and z axes are orthogonal with the midline of the AC/PC plane. The CT or MRI images are scanned, such that the slices are orthogonal to the AC/PC plane and thus obtained or generated under the proper coordinate system. One way to insure proper positioning of the head ring 48, is to line the head ring along the AC/PC plane by utilizing the tragus of the ear and the canthus of the eye as the proper landmarks to provide proper AC/PC alignment. Alternatively, existing software packages available in the art enable the head ring or head frame 48 to be positioned on the patient so that the computer will simply automatically determine where the AC/PC plane is and align the image slices so that they are orthogonal to the AC/PC plane. Thus, everything is typically referenced off of the AC/PC plane either by proper initial positioning of the head ring 48 or by correcting for roll, pitch and yaw using known software, such that everything is in the AC/PC coordinate system.

Once the patient 14 has been imaged at block 134, image data is loaded into the work station 34. This image data may also include the preoperative MRI data acquired before the head ring 48 was positioned on the patient and used for preoperative planning. This image data may also be merged or fused with the image data captured with the head ring 48 as previously discussed and known in the art. After imaging, the procedure proceeds to block 136 where each transmitter coil array 64 is attached to the stereotactic frame 48. Again, each transmitter coil array 64 can only fit on to the stereotactic frame 48 in one pre-specified unique manner with each transmitter coil arrays 64 having a unique site 76, 78, and 80. Additionally, if the fiducial head cage 86 was employed during imaging, the fiducial head cage is removed prior to attaching the transmitter coil arrays 64. After the transmitter coil arrays 64 are attached to the stereotactic frame 48, the transmitter coil arrays 64 are also coupled to the navigation probe interface 66 and the patient 14 is positioned on the OR table 60.

The method then proceeds to block 138 where auto registration between the preacquired images and navigable patient space is performed. In this regard, if the fiducial head cage 86 was not utilized during the imaging 134, the work station 34 will identify the unique hole positions on the stereotactic frame 48 from the preacquired scan using known pattern recognition software. Once the work station 34 identifies these locations, and with knowing the size and shape of the stereotactic frame 48 and where each transmitter coil array 64 is located on the stereotactic frame 48, the work station 34 can correlate and create a translation map between all points in the preacquired images and the corresponding points in the patient's anatomy or patient space. After this translation map is automatically established, whenever a tracked lead 70 or other device is used, the work station 34, in combination with the electromagnetic tracking system 62 uses the translation map to identify the corresponding point on the preacquired image, which is displayed on display 36. This identification is generally known as navigation or localization. An icon representing the localized point or instrument 70 may be superimposed over the preacquired images and illustrated on the display 36, as well as on any intraoperative images taken by the imaging device 12.

If the fiducial head cage 86 was utilized during imaging 134, further refined registration accuracy can be obtained since the fiducial head cage 86 encompasses more volume within the anatomy of interest. In other words, the fiducial rods 88 are located throughout the volume of interest and again have known locations. Since the positions and angles of the rods 88 are known, the work station 34 can again identify and correlate the preacquired images, via using known pattern recognition software with the patient's anatomy in the patient space. Also, because the fiducial head cage 86 is attached to the rigidly coupled stereotactic frame 48, automatic registration is again achievable with a high level of accuracy.

Briefly, to enable navigation, the stereotactic navigation system 10 must be able to detect both the position of the patient's anatomy and the position of the lead 70 or other surgical instrument. Knowing the location of these two items allows the stereotactic navigation system 10 to compute and display the position of the lead 70 in relation to the patient 14 on the preacquired or intraoperative images. The electromagnetic tracking system 62 is employed to track both the position of the lead 70 and the anatomy of the patient 14 simultaneously.

The electromagnetic tracking system 62 essentially works by positioning the transmitter coil array 64 adjacent to the patient space to generate a low energy magnetic field generally referred to as a navigation field. Because every point in the navigation field or patient space is associated with a unique field strength, the electromagnetic tracking system 62 can determine the position of the lead 70 by measuring the field strength at the electromagnetic sensor 68 location. Since the transmitter coil array 64 is attached directly to the stereotactic frame 48, the location of the patient 14 is also continuously monitored. This eliminates the need for a separate dynamic reference frame, which is typically used with conventional electromagnetic navigation systems. By eliminating the use of a dynamic reference frame, any errors resulting in the use of the dynamic reference frame is also eliminated by the stereotactic navigation system 10.

Again, the auto registration method is a process of determining how to correlate the real-time position of the lead 70 relative to the preacquired images 134 or real-time images generated by the imaging device 12. Since the work station 34 can identify the corresponding points, such as the fiducial hole patterns or the fiducial rods 88 in the preacquired images, the stereotactic navigation system 10 is able to analyze a relationship between these points and the corresponding points on the patient's anatomy, which are known, via affixing the transmitter coil arrays 62 to the unique sites 76, 78, and 80. The stereotactic navigation system 10 analyzes the relationship between these two sets of points and computes a match, which correlates every point in the image data and its corresponding point in the patient's anatomy or patient space. The points that are automatically selected and identified by the work station 34 are sometimes referred to as fiducial points or landmarks. Since the transmitter coil arrays 64 are attached to the stereotactic frame 48, at these fiducial points or locations, which is directly and rigidly fixed to the patient 14, any movement of the patient is tracked, via the transmitter coil array 64, thereby again eliminating the need for a dynamic reference frame, which is typically used in electromagnetic navigation systems.

Once auto registration has been performed at block 138, the process proceeds to block 140 where the physician or the work station 34 automatically identifies the target 114 from the preacquired images, atlas images or merged images. Once the target 114 has been selected using a device 38, the method proceeds to block 142 where the x, y, and z-stages 96, 98, and 100 are adjusted as guided by the work station 34. Again, since each stage 96, 98, and 100 include an electromagnetic sensor 68, the location of each stage can be monitored and tracked, via the electromagnetic tracking system 62. This enables the work station 34 to provide real-time feedback, as illustrated in FIG. 10, of the location of the target 114 relative to the stereotactic frame centroid 110. Again, the adjustment can be performed manually using knobs or sliders, semi-manually using the power driven screw driver 104 or fully automated using motors associated with each stage and driven by the work station 34. Once each stage is aligned along the x-axis 90, y-axis 92, and z-axis 94, the work station 34 provides an indication to the user, via a visual display or an audible alarm identifying that the target 114 has been set, via the adjusted stages.

The method then proceeds to block 144 where the surgeon creates a planned entry point 128 using the arc 50 along with the guide tube or tool holder 124. The planned entry point 144 is determined upon review of the preoperative scans and/or atlas maps and may be performed preoperatively or intraoperatively, depending on the particular procedure and result of burr hole placements. Again, the trajectory may also be selected by the work station 34 based upon analysis of the preacquired images and upon the use of atlas maps. Once the planned entry has been selected at 144, the method proceeds to block 146 where the currently aligned trajectory is guided to the planned trajectory utilizing the arc 50 and tool holder 124, which are each monitored, via electromagnetic sensors 68. The tool holder 124 may also be a motorized tool holder that drives the DBS lead 70 or microelectrode into the brain through an inserter or cannula, such that the motorized tool holder provides a read out on how deep the lead 70 penetrates the brain by reading a depth off of a stepper motor in the micro range. This information, along with the sensor 68 information provides visual alignment of the aligned trajectory with the planned trajectory or entry point 128 that can be displayed on screen 126, illustrated in FIG. 12.

From block 146, the method proceeds to block 148 where micro-electro recording (MER) electrodes are inserted into a cannula, such as the tracked cannula 87, as shown in FIG. 5b. following the trajectory and target adjustment. As previously discussed, the MER electrodes are very high impedance electrodes that are utilized to detect electrical activity of cells in the brain. These electrical activities typically have very distinct firing patterns which can be used to confirm proper positioning of the MER electrodes. In order to verify that the MER electrodes have reached the target, the MER electrodes may be positioned within the stylet or cannula 87 such that the EM sensor 68 located at the distal end of the substantially rigid cannula 87 enables localization up to at least the stylet location within the brain using the electro magnetic navigation system 62. Since the MER electrode is extremely fine, the electrode extends out past the stylet and generally will not include the EM sensor. However, since the distance of the MER electrode extending past the stylet is known, a simple calculation can be made to determine the distal end of the MER electrode. A representation of the electrode can then be superimposed onto the preacquired image which shows the electrode reaching the target, via display 36. In order to provide a further level of accuracy, an interoperative image can be taken by the imaging device 12 once the MER electrode has been positioned to confirm that the MER electrode has reached the target site.

Once the MER electrode has reached the target site and verified at block 148, the method proceeds to block 150 where either the integrated DBS lead 70 or lead 89 is implanted after the MER electrode has been removed from cannula 87. Again, tracking of the lead 70 or 89 is possible, via an electromagnetic sensor 68 attached to the integrated lead 70 or cannula 87. Finally, at block 152, contact positions of the DBS lead 70 or 89 can be verified in relation to the target 114, via direct localization utilizing the navigation system 62 and the preacquired images. Alternatively, or in addition, an interoperative image may be captured, via the imaging device 12 to provide a real time actual image confirming proper placement of the lead 70 or 89.

Again, the stereotactic navigation system 10 provides significant advances over existing systems. In this regard, the stereotactic navigation system 10 eliminates the need for interoperative fluoroscopic images of the brain, since the navigation system 62 provides real-time tracking and feedback of lead placement. Fluoroscopic images using each device 12 may, of course, be utilized should further real-time assurance of the lead placement be desired. The stereotactic navigation system 10 also reduces the need for providing significant knowledge about stereotactic frame or image guided surgery, since there is no manual registration processes and automatic registration results because of the positioning of the transmitter coil arrays 64, relative to the stereotactic frame 48. This type of configuration also eliminates the need for an additional dynamic reference frame, which would track the position of the patient 14, since the transmitter coil arrays 64 are attached directly to the stereotactic frame 48, which is attached directly to the patient 14. The stereotactic frame 48 also does not require gradiations or scaling, which can limit the accuracy of target and entry point placements, providing further enhanced accuracy and freedom of movement and adjustment. Additionally, the work station 34 provides real-time feedback regarding adjustment of the target and entry points, thereby eliminating the need for manual calculations and potential user error in making the adjustments, since the adjustments are confirmed, via the work station and illustrated, via the display.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A stereotactic navigation system for navigating an instrument to a target site within a patient, the stereotactic navigation system comprising:
   a stereotactic head frame defining a navigable patient space and configured to be coupled to the patient and used to assist in guiding the instrument to the target site;
   a tracking system with a plurality of tracking devices operable to be tracked;
   a first sub-plurality of the plurality of tracking devices, configured to be coupled to the stereotactic head frame for use in tracking an instrument location of the instrument;
   a processor system for registering the navigable patient space to acquired image data of the patient; and
   an adjustment system configured to be coupled to the stereotactic head frame and including a stage to which a second sub-plurality of the plurality of tracking devices is configured to be connected, the adjustment system is configured for adjusting a location and orientation of the instrument relative to the target site by adjusting the stage, the adjustment system automatically adjusting the stereotactic head frame via a real-time closed loop feedback with the processor system and the stereotactic head frame.

2. The stereotactic navigation system of claim 1, wherein the stage of the adjustment system includes a plurality of stages, wherein each stage is configured to be tracked with the second sub-plurality of the plurality of tracking devices and wherein each stage is movable along a corresponding plurality of mutually orthogonal axes, wherein at least a first stage of the plurality of stages automatically is adjusted by the real-time closed loop feedback.

3. The stereotactic navigation system of claim 2, wherein at least the first stage is automatically adjusted by a robotic device.

4. The stereotactic navigation system of claim 1, wherein the stage of the adjustment system includes first, second and third stages movable along corresponding and mutually orthogonal first and second axes, the first, second and third stages automatically adjustable by a robotic device.

5. The stereotactic navigation system of claim 1, wherein the instrument is selected from at least one of a catheter, a guide wire, a stylet, a lead, a cannula, an insert, a needle, a biopsy tube, and a combination thereof.

6. The stereotactic navigation system of claim 1, wherein the stage of the adjustment system includes a plurality of stages movable along a corresponding plurality of mutually orthogonal axes, at least a first stage of the plurality of stages adjustable by a user based on directions received by the work station.

7. The stereotactic navigation system of claim 1, in combination with the instrument, the instrument including a deep brain stimulation (DBS) lead, the DBS lead including a plurality of electromagnetic sensors for tracking the position of the lead.

8. The stereotactic navigation system of claim 1, in combination with the instrument, the instrument including a cannula having at least one tracking microelectrode and a deep brain stimulation lead passing through the cannula.

9. The stereotactic navigation system of claim 1, wherein the adjustment system automatically adjusts the stereotactic head frame based on the acquired image data.

10. A stereotactic navigation system for navigating an instrument to a target site within a patient, the stereotactic navigation system comprising:
    a stereotactic head frame defining a navigable patient space and configured to be coupled to the patient and used to assist in guiding the instrument to the target site;
    a tracking device configured to be coupled to the stereotactic head frame for use in tracking the instrument;
    a processor system for registering the navigable patient space to acquired image data of the patient; and
    an adjustment system configured to be tracked and coupled to the stereotactic head frame, the adjustment system configured for adjusting a location and orientation of the instrument relative to the target site, the adjustment system automatically adjusting the stereotactic head frame via a real-time closed loop feedback with the processor system and the stereotactic head frame;
    wherein at least the first stage is automatically adjusted by a robotic device and the robotic device includes an automated screw driver configured to drive a movement of at least the first stage.

11. The stereotactic navigation system of claim 10, wherein the screw driver includes a high gear setting for coarse adjustment and a low gear setting for fine adjustment.

12. A stereotactic navigation system for navigating an instrument to a target site within a patient, the stereotactic navigation system comprising:
    a stereotactic head frame defining a navigable patient space and configured to be coupled to the patient and used to assist in guiding the instrument to the target site;
    a tracking device configured to be coupled to the stereotactic head frame for use in tracking the instrument;
    a processor system for registering the navigable patient space to acquired image data of the patient;
    an adjustment system configured to be tracked and coupled to the stereotactic head frame, the adjustment system configured for adjusting a location and orientation of the instrument relative to the target site, the adjustment system automatically adjusting the stereotactic head frame via a real-time closed loop feedback with the processor system and the stereotactic head frame; and
    a coupling device including a first coupling portion defined by the stereotactic head frame and a second coupling portion defined by the tracking device, the second coupling portion being complementary to the first coupling portion;
    wherein the processor system is configured to recognize a position and an orientation of the first coupling portion and relate the position and orientation of the first coupling portion to a position and orientation of the tracking device to register the navigable patient space to the image data.

13. The stereotactic navigation system of claim 12, wherein the tracking device is configured to be removably coupled to the stereotactic head frame at a unique location on the stereotactic head frame, the tracking device is further configured to track the position of the instrument relative to the stereotactic head frame and to be removed from the stereotactic head frame during acquisition of the image data of the patient with the stereotactic head frame.

14. The stereotactic navigation system of claim 13, wherein the tracking device includes a plurality of removable transmitter coil arrays, each configured to generate an electromagnetic navigation field.

15. The stereotactic navigation system of claim 14, wherein the coupling device includes an attachment device associated with each transmitter coil array configured to be used to removably couple each transmitter coil array at its corresponding unique location.

16. The stereotactic navigation system of claim 14, wherein each transmitter coil array comprises three orthogonal coils.

17. The stereotactic navigation system of claim 14, wherein the processor system is configured to automatically register image data with the navigable patient space defined by the stereotactic head frame.

18. The stereotactic navigation system of claim 17, further comprising an imaging device configured to capture the image data of the navigable patient space within the patient.

19. The stereotactic navigation system of claim 18, further comprising a second tracking device associated with the instrument and configured to track a position of the instrument relative to the stereotactic head frame and a display configured to display the image data of the navigable patient space with a superimposed icon of the tracked instrument.

20. A stereotactic navigation system for navigating an instrument to a target site within a patient, the stereotactic navigation system comprising:
a stereotactic head frame defining a navigable patient space and configured to be coupled to the patient and used to assist in guiding the instrument to the target site;
an imaging device configured to capture image data of the navigable patient space and of the stereotactic head frame;
a first tracking device removably coupled to the stereotactic head frame and configured to track the position of the instrument relative to the stereotactic head frame;
an adjustment system configured to be tracked and coupled to the stereotactic head frame, the adjustment system including a plurality of stages configured to be tracked each with at least a second tracking device and each of the plurality of stages movable along a corresponding plurality of mutually orthogonal axes, the adjustment system configured for adjusting a location and orientation of the instrument relative to the target site; and
a tracking system including the first tracking device and the second tracking device to track locations of the first tracking device and the second tracking device;
a work station having a processor, a display screen and a user interface, the display screen configured to display the image data and a plurality of adjustment scales corresponding to the plurality of stages for adjusting the location and orientation of the instrument via the user interface, the work station configured to receive the image data from the imaging device, the work station further configured to automatically register the image data with the navigable patient space.

21. The stereotactic navigation system of claim 20, wherein the tracking device is configured to be removed from the stereotactic head frame during imaging of the patient.

22. The stereotactic navigation system of claim 21, wherein the tracking device includes a plurality of removable transmitter coil arrays, each configured to generate an electromagnetic navigation field.

23. The stereotactic navigation system of claim 22, wherein the plurality of trackable stages are configured to adjust the stereotactic head frame along an x-axis, a y-axis, and a z-axis.

24. The stereotactic navigation system of claim 23, further comprising a tracking sensor associated with each axis and configured to track movement of the stereotactic head frame along each axis using the tracking device.

25. The stereotactic navigation system of claim 20, further comprising a tool guide adjustably coupled to the stereotactic head frame and configured to align an entry point of the instrument to the target site.

26. The stereotactic navigation system of claim 25, further comprising;
at least one tracking sensor associated with the tool guide;
wherein the at least one tracking sensor is configured to identify a location of the entry point relative to the target site.

27. A stereotactic navigation system for navigating an instrument to a target site within a patient, the stereotactic navigation system comprising:
a stereotactic head frame defining a navigable patient space and configured to be coupled to the patient and used to assist in guiding the instrument to the target site;
an imaging device configured to capture image data of the navigable patient space and of the stereotactic head frame;
a tracking device removably coupled to the stereotactic head frame and configured to track the position of the instrument relative to the stereotactic head frame;
an adjustment system configured to be coupled to the stereotactic head frame, the adjustment system including a plurality of stages each configured to be movable along a corresponding plurality of mutually orthogonal axes, the adjustment system configured for adjusting a location and orientation of the instrument relative to the target site;
a tracking sensor associated with each of the plurality of mutually orthogonal axes and configured to track movement of the stereotactic head frame along each of the plurality of mutually orthogonal axes using the tracking device; and
a work station having a processor, a display screen and a user interface, the display screen configured to display the image data and a plurality of adjustment scales corresponding to the plurality of stages for adjusting the location and orientation of the instrument via the user interface, the work station configured to receive the image data from the imaging device, the work station further configured to automatically register the image data with the navigable patient space;
wherein the work station is further configured to identify the target site on the display screen and further configured to identify the location of a centroid of the stereotactic head frame relative to the target site on the display screen.

28. The stereotactic navigation system of claim 27, wherein the work station is further configured to provide real-time feedback of the adjustment of the stereotactic head frame and display the real-time feedback of the adjustment on the display screen.

29. A method for performing image guided stereotactic navigation, the method comprising:
attaching a stereotactic head frame defining navigable patient space on a patient;
capturing image data of the navigable patient space with the attached stereotactic head frame;

attaching a first tracking device to the stereotactic head frame;

automatically registering the image data with the navigable patient space;

coupling an adjustment system to the stereotactic head frame, wherein the adjustment system includes a stage to which a second tracking device is connected, and wherein the adjustment system is configured for adjusting a location and orientation of an instrument relative to a target site by adjusting the stage;

adjusting the adjustment system via a real time closed loop feedback between a processor and the tracking device; and tracking the second tracking device while adjusting the adjustment system.

30. The method of claim 29, wherein adjusting the stereotactic head frame includes automatically adjusting the stereotactic head frame using a robotic device.

31. The method of claim 29, wherein adjusting the stereotactic head frame includes adjusting the stereotactic head frame via a user interface communicating with the processor.

32. The method of claim 29, wherein adjusting the stereotactic head frame includes:

moving a screen slider displayed on a display screen connected to the user interface; and moving a stage coupled to the stereotactic head frame, the stage corresponding to the screen slider.

33. The method of claim 32, further comprising identifying a target site in the image data on the display screen.

34. The method of claim 33, further comprising selecting a planned entry point for delivering an instrument to the target site.

35. The method of claim 34, further comprising displaying a representation of the instrument superimposed on the image data in relation to the target site.

36. The method of claim 32, further comprising identifying a target site in the image data on the display screen and identifying a location of a centroid of the stereotactic head frame relative to the target site on the display screen.

* * * * *